US012629212B2

(12) United States Patent
Blau

(10) Patent No.: US 12,629,212 B2
(45) Date of Patent: May 19, 2026

(54) DETERMINING RELATIVE 3D POSITIONS AND ORIENTATIONS BETWEEN OBJECTS IN 2D MEDICAL IMAGES

(71) Applicant: metamorphosis GmbH, Altenbeken (DE)

(72) Inventor: Arno Blau, Staufen (DE)

(73) Assignee: metamorphosis GmbH, Altenbeken (DE)

( * ) Notice: Subject to any disclaimer, the term of this patent is extended or adjusted under 35 U.S.C. 154(b) by 570 days.

(21) Appl. No.: 17/757,304

(22) PCT Filed: Dec. 16, 2020

(86) PCT No.: PCT/EP2020/086503
§ 371 (c)(1),
(2) Date: Jun. 14, 2022

(87) PCT Pub. No.: WO2021/122804
PCT Pub. Date: Jun. 24, 2021

(65) Prior Publication Data
US 2022/0398776 A1     Dec. 15, 2022

(30) Foreign Application Priority Data

Dec. 17, 2019    (EP) ..................................... 19217245

(51) Int. Cl.
*A61B 34/20*         (2016.01)
*A61B 6/00*          (2024.01)
(Continued)

(52) U.S. Cl.
CPC .......... *A61B 34/20* (2016.02); *A61B 17/1703* (2013.01); *A61B 17/1717* (2013.01);
(Continued)

(58) Field of Classification Search
CPC ...... A61B 2090/3764; A61B 2090/376; A61B 34/20; A61B 34/10; A61B 34/25;
(Continued)

(56) References Cited

U.S. PATENT DOCUMENTS

| | | | |
|---|---|---|---|
| 8,170,717 B2 * | 5/2012 | Sutherland ............. | A61B 34/35 901/14 |
| 2012/0106819 A1 * | 5/2012 | Fernandez Oca ...... | A61B 34/10 382/132 |

(Continued)

FOREIGN PATENT DOCUMENTS

| | | |
|---|---|---|
| JP | 2023506511 A | 3/2024 |
| JP | 7475082 B2 | 4/2024 |

(Continued)

OTHER PUBLICATIONS

EPO, International Search Report issued in IA No. PCT/EP2020/086503, mailed Feb. 22, 2021.
(Continued)

*Primary Examiner* — Marcela I. Shirsat
(74) *Attorney, Agent, or Firm* — LNK LAW, PLLC

(57) ABSTRACT

Systems and methods are provided for processing X-ray images, wherein the methods are implemented as a software program product executable on a processing unit of the systems. Generally, an X-ray image is received by the system, the X-ray image being a projection image of a first object and a second object. The first and second objects are classified and a respective 3D model of the objects is received. At the first object, a geometrical aspect like an axis or a line is determined, and at the second object, another geometrical aspect like a point is determined. Finally, a spatial relation between the first object and the second object is determined based on a 3D model of the first object, a 3D model of the second object, and the information that the
(Continued)

point of the second object is located on the geometrical aspect of the first object.

19 Claims, 27 Drawing Sheets

(51) Int. Cl.

| | |
|---|---|
| *A61B 17/17* | (2006.01) |
| *A61B 17/56* | (2006.01) |
| *A61B 34/00* | (2016.01) |
| *A61B 34/10* | (2016.01) |
| *A61B 90/00* | (2016.01) |
| *G06F 18/24* | (2023.01) |
| *G06T 7/00* | (2017.01) |
| *G06T 7/13* | (2017.01) |
| *G06T 7/30* | (2017.01) |
| *G06T 7/60* | (2017.01) |
| *G06T 7/70* | (2017.01) |
| *G06T 7/73* | (2017.01) |
| *G06T 17/00* | (2006.01) |

(52) U.S. Cl.
CPC ...... *A61B 17/1725* (2013.01); *A61B 17/1757* (2013.01); *A61B 34/10* (2016.02); *A61B 34/25* (2016.02); *G06F 18/24* (2023.01); *G06T 7/13* (2017.01); *G06T 7/30* (2017.01); *G06T 7/60* (2013.01); *G06T 7/74* (2017.01); *G06T 7/75* (2017.01); *G06T 17/00* (2013.01); *A61B 6/487* (2013.01); *A61B 2017/564* (2013.01); *A61B 2034/102* (2016.02); *A61B 2034/105* (2016.02); *A61B 2034/2065* (2016.02); *A61B 2034/2068* (2016.02); *A61B 2034/252* (2016.02); *A61B 2090/3764* (2016.02); *G06T 7/0012* (2013.01); *G06T 7/70* (2017.01); *G06T 7/73* (2017.01); *G06T 2207/10116* (2013.01); *G06T 2207/30012* (2013.01); *G06T 2207/30052* (2013.01); *G06V 2201/033* (2022.01); *G06V 2201/034* (2022.01)

(58) Field of Classification Search
CPC .......... A61B 2017/564; A61B 17/1703; A61B 17/1717; A61B 17/1725; A61B 17/1757; A61B 2034/102; A61B 2034/105; A61B 2034/2065; A61B 2034/252; A61B 2034/2068; A61B 6/487; G06T 7/74; G06T 7/30; G06T 7/75; G06T 7/13; G06T 7/60; G06T 7/0012; G06T 7/70; G06T 7/73; G06T 17/00; G06T 2207/10116; G06T 2207/30012; G06T 2207/30052; G06T 2207/10121; G06T 2207/30008; G06F 18/24; G06V 2201/034; G06V 2201/033
USPC ............................................ 382/182; 606/97
See application file for complete search history.

(56) References Cited

U.S. PATENT DOCUMENTS

| | | |
|---|---|---|
| 2015/0216614 A1 | 8/2015 | Simon et al. |
| 2020/0275824 A1* | 9/2020 | Tata .................... A61B 1/0052 |
| 2020/0323506 A1* | 10/2020 | Blau ........................ G06T 7/60 |
| 2021/0248779 A1* | 8/2021 | Blau ...................... G06T 17/00 |

FOREIGN PATENT DOCUMENTS

| | | |
|---|---|---|
| WO | 2018034661 A2 | 2/2018 |
| WO | 2019077388 A1 | 4/2019 |

OTHER PUBLICATIONS

Giulio D., et al. "Intra operative fiducial-based CT/fluoroscope image registration framework for image-guided robot-assisted joint fracture surgery", International Journal of Computer Assisted Radiology and Surgery, May 2017, pp. 1383-1397, vol. 12, No. 8, Springer DE.

* cited by examiner

10.O

General

DETERMINING RELATIVE 3D POSITIONS AND ORIENTATIONS BETWEEN OBJECTS IN 2D MEDICAL IMAGES

CROSS-REFERENCE TO RELATED APPLICATION

This application is a U.S. National-Stage entry under 35 U.S.C. § 371 based on International Application No. PCT/EP2020/086503, filed Dec. 16, 2020, which was published under PCT Article 21(2) and which claims priority to European Application No. 19217245.0, filed Dec. 17, 2019, which are all hereby incorporated in their entirety by reference.

FIELD OF INVENTION

The invention relates to the fields of artificial intelligence and computer assisted surgery. In particular, the invention relates to a device and a method for determining 3D representations and relative 3D positions and relative 3D orientations between objects based on an X-ray projection image. The method may be implemented as a computer program executable on a processing unit of the device.

BACKGROUND OF THE INVENTION

In orthopedics or orthopedic trauma surgery or spinal surgery, it is a common task to aim for a target object or target structure (as part of a target object) with a relatively thin instrument. Target structures may be anatomical (e.g., a pedicle) or parts of other instruments or implants (e.g., a distal locking hole of a long antegrade intramedullary nail). In general, the goal may be to determine the 3D relative position and 3D relative orientation between instrument and target object. Based on available intraoperative 2D imaging techniques, this may be challenging. It is particularly difficult if the precise geometry of the target object is unknown, and/or if the instrument is known, but not uniquely localizable in 3D space based on the 2D X-ray image.

For surgical procedures, preoperative CT scans may be performed, which allow a more precise planning of the procedure. This is the case, for instance, when operating within a complex 3D structure, or when drilling or placing screws within narrow anatomical structures or in the vicinity of critical structures (e.g., spinal cord, nerves, aorta). Typical examples of such procedures are the placements of sacro-iliac or pedicle screws. When the target structure is a tool or an implant, its 3D geometry is typically known: An example is the distal locking procedure, where a 3D model of, or 3D information about the target object (nail), and in particular the target structure "distal locking hole" (a cylinder) is available.

However, for the surgeon to utilize this 3D information and to apply it to intraoperative 2D X-ray images requires a high level of spatial perception and imagination.

In some cases and for some procedures, it may be possible to determine, for instance, the direction of drilling by aligning it with a particular viewing direction of the imaging equipment (e.g., for the distal locking procedure, a true medial-lateral view). Yet ensuring that the drilling indeed proceeds precisely along this direction is not generally possible. This will now be illustrated for the example of distal locking of a long antegrade intramedullary nail.

In the conventional distal locking procedure of an antegrade nail, the surgeon moves the C-arm into a true lateral position, which means that the hole to be locked appears perfectly round in the X-ray image. This positioning is tedious and time-consuming, possibly taking several minutes, because it is done iteratively: it typically requires the acquisition of 5 to 20 X-ray images with corresponding re-adjustments of the C-arm. A faster way of achieving this positioning is to use the fluoroscopic mode of the C-arm (producing a continuous X-ray video stream), but this leads to a higher X-ray dose.

Moreover, in order to ensure high accuracy for distal locking, not only must the hole appear round, but it also must be close to the center of the X-ray image. However, in practice, once the hole appears round enough in the X-ray image, this C-arm position is typically used for distal locking even if the hole is not close to the center of the X-ray image. Due to a cone shape of the X-ray beam fan, the direction of X-ray beams is inclined the further the beams are away from the center of the X-ray image. Thus, drilling through a hole should be in the direction of the focal point of the X-ray source and not parallel to a center line between X-ray source and detector.

In a next step, the tip of the drill may be placed on the intended drill location and an X-ray image is acquired. Here, the drill may intentionally be held at an oblique angle, i.e., not in the direction of the locking trajectory, so that the power drill and the surgeon's hand do not occlude the view. The goal is to place the drill such that, in the X-ray image, the drill tip appears in the center of the (round) locking hole. This is also done iteratively, typically requiring 5 to 10 iterations and X-ray images.

Once this has been achieved with sufficient accuracy, the drill is aligned with the target trajectory, leaving the drill tip in place. This alignment is typically not checked with X-rays because at this angle, the power drill and the surgeon's hand would occlude the view. Hence, the surgeon uses the C-arm's position as a guide and attempts to align the drill parallel to the "C". Achieving and then maintaining such alignment during drilling requires a fairly high level of manual dexterity. Moreover, the surgeon typically does not observe that he/she should aim at the focal point of the X-ray source. The error introduced by neglecting to aim at the focal point becomes the larger the further the locking hole appears from the center of the X-ray image. A typical error is in the range of 1-2 mm at the target point (the locking hole). This is close to the limit of 3 mm, beyond which distal locking fails for most nailing systems. All of this means that, especially for less experienced or skilled surgeons, abortive drilling attempts occur.

Because generally more than one hole needs to be locked, this entire procedure must be repeated for each hole. Thus, completing the entire locking procedure for a nail is typically very time-consuming, requires many X-ray images, and often involves abortive drilling attempts. This means that distal locking is one of the most frustrating procedures in the area of osteosynthesis. This occasionally leads to the shortcut of employing a short instead of long nail, which in turn leads to worse patient outcomes and a significant number of revision surgeries.

For this reason, some manufacturers offer a flexible mechanical solution (hereafter called "long aiming device") that adjusts to the bending of the nail in the medullary canal. While a long aiming device simplifies the procedure, its application is still not straightforward because X-ray images showing the long aiming device must be interpreted correctly and the C-arm position adjusted accordingly. Only after correct adjustment of the C-arm may the long aiming device be adjusted properly.

EP 2801320 A1 proposes a concept where a reference body with metallic markers at a fixed and known position relative to the long aiming device is detected, and the imaging direction onto the reference body is determined. Based on that, the system may give instructions on how to adjust the C-arm imaging device. The disadvantage of such a system is that the X-ray image must contain the reference body. For the adjustment of a long aiming device in case of an antegrade femur nail with locking holes in lateral direction, US 2013/0211386 A1 uses a reference body in order to determine the bending of the nail in ML direction and in AP direction, respectively.

Beyond distal locking, in order to increase the safety and accuracy of minimally invasive procedures in general, it is necessary for the surgeon to have access to the necessary intraoperative 3D information, i.e., the relative 3D position and 3D orientation between an instrument and a target object/structure or between a plurality of anatomical objects. This information may be displayed by a tracking-based navigation system, which requires preoperative 3D imaging and then intraoperatively registers the intraoperative 2D imaging data with the preoperative 3D data. Another alternative is the use of a database containing 3D information about the target object (e.g., an implant database) and additional tools, often in the form of additional hardware (e.g., a long aiming device). These systems are often unwieldy, time-consuming and tedious in setup and intraoperative use, and typically expensive. Hence, for all these disadvantages, navigation-based systems are not always available or even feasible for use in orthopedics and trauma. The same comments apply to systems for intraoperative 3D imaging (e.g., O-arm, 3D C-arm), which also add a high X-ray dose.

This highlights the need for a noninvasive and easy-to-use system that is capable of providing intraoperative 3D information without tracking system and without requiring any additional hardware components. The present invention proposes systems and methods, which require only a computer and display and/or loudspeaker, to process intraoperative 2D images. Both techniques that utilize deterministic 3D data of the target object (e.g., in the form of 3D preoperative imaging data or 3D model data of an implant) and those that do not require such data are presented.

SUMMARY OF THE INVENTION

It is preferable to work without any reference bodies or other additional hardware (e.g., an aiming device) because it simplifies product development (e.g., if employing a new implant), is more cost-effective, allows an operating room workflow that more closely resembles the typical workflow, and eliminates the added uncertainties which would be introduced by a mechanical interface for a reference body.

The invention as described herein suggests combining knowledge about the X-ray image generation process with artificial intelligence (in the form of so-called deep morphing and/or the utilization of a neural net) instead of any reference body for providing information needed when performing a treatment of, for example, a fractured bone. It may thus be seen as an object of the invention to provide a device and/or a method enabling 3D representations and determining relative 3D positions and relative 3D orientations between multiple objects at least partially visible in an X-ray projection image. Here, an object may be any object visible in an X-ray image, e.g. an anatomical structure, an implant, a surgical tool, and/or a part of an implant system.

The term "3D representation" may refer to a complete or partial description of a 3D volume or 3D surface, and it may also refer to selected geometric aspects, such as a radius, an axis, a plane, or the like. It may be possible to determine complete 3D information about the 3D surface or volume of an object, but in many applications, it may be sufficient to determine only selected geometric aspects.

Throughout this application, the terms "localize" and "localization" mean a determination of the 3D orientation of an object and a determination of the 2D spatial position of the projection of that object onto the image plane. The imaging depth (which is the distance of the object from the image plane), on the other hand, is estimated (with some uncertainty) based on a priori information about typical constellations of objects in the operating room, e.g., relative positions of implant, patient, and imaging device. For most purposes of this invention, such an estimated imaging depth is sufficient. Some applications may require determining the imaging depth more precisely, which is possible in certain cases, as discussed further below.

According to an embodiment, a 3D reconstruction (i.e., a determination of a 3D representation) and localization of an object is provided whose shape and appearance have some variability. This can be done based on a single X-ray image or, for increased accuracy, a plurality of X-ray images. A 3D representation and localization of related objects like anatomical structures, implants, surgical tools, and/or parts of implant systems, even if not or only partially visible in the X-ray image, may also be provided.

According to an embodiment, a determination of the relative 3D positions and 3D orientations between a plurality of objects is provided, even if localization of at least one of the objects individually would not be possible with sufficient accuracy. This may be achieved by utilizing a priori geometric information about the relative position and/or orientation between aspects of at least two objects, and possibly also restricting the range of allowable X-ray imaging directions. Possible clinical applications may include free-hand distal locking, the placement of sacroiliac (SI) or pedicle screws, and an evaluation of anatomical reduction of fractures.

It is noted that the image data of the processed X-ray image may be received directly from an imaging device, for example from a C-arm based 2D X-ray device, or alternatively from a database. Aspects of the invention may also be used to process medical images acquired using other imaging modalities, such as ultrasound or magnetic resonance imaging.

The system suggested in accordance with an embodiment comprises at least one processing unit generally configured to execute a computer program product including sets of instructions causing the device (i) to receive an X-ray projection image whose characteristics depend on imaging parameters, (ii) to classify at least one object in the X-ray projection image, (iii) to receive a model of the classified object, and (iv) to determine a 3D representation of the classified object and to localize the classified object with respect to a coordinate system, by matching a virtual projection of the model to the actual projection image of the classified object. This process may consider the characteristics of the X-ray imaging method. In particular, the fact may be considered that the intercept theorem applies, as discussed in the examples later.

The X-ray projection image may represent an anatomical structure of interest, in particular, a bone. The bone may for example be a bone of a hand or foot, a long bone of the lower extremities, like the femur and the tibia, and of the upper extremities, like the humerus, or a vertebra, or a pelvis. The image may also include an artificial object like a surgical tool (e.g., a drill) or a bone implant being already inserted into or affixed to the imaged anatomical structure of interest.

In the context of the invention, it will be differentiated between an "object" and a "model". The term "object" will be used for a real object, e.g., for a bone or part of a bone or another anatomical structure, or for an implant like an intramedullary nail, a bone plate or a bone screw, or for a surgical tool like a sleeve, k-wire, scalpel, drill, or aiming device, which may be connected to an implant. An "object" may also describe only part of a real object (e.g., a part of a bone), or it may be an assembly of real objects and thus consist of sub-objects. In order to emphasize that an object is a sub-object of another object, it may also be called a "structure". For instance, a "locking hole" of a nail may be considered a structure (or sub-object) of the object "nail". As another example, a "pedicle" of a vertebra may be considered a structure of the object "vertebra". Nevertheless, a structure itself (like the pedicle) may also be referred to simply as "object".

The term "model" will be used for a virtual representation of an object (or a sub-object, or a structure). For example, a data set defining the shape and dimensions of an implant may constitute a model of an implant. As another example, a 3D representation of anatomy as generated for example during a diagnostic procedure may be taken as a model of a real anatomical object. It should be noted that a "model" may describe a particular object, e.g., a particular nail or the left femur of a particular patient, or it may describe a class of objects, such as a femur in general, which have some variability. In the latter case, such objects may for instance be described by a statistical shape or appearance model. It may then be an aim of the invention to find a 3D representation of the particular instance from the class of objects that is depicted in the acquired X-ray image. For instance, it may be an aim to find a 3D representation of a vertebra depicted in an acquired X-ray image based on a general statistical shape model of vertebrae. It may also be possible to use a model that contains a discrete set of deterministic possibilities, and the system would then select which one of these best describes an object in the image. For instance, there could be several nails in a database, and an algorithm would then identify which nail is depicted in the image (if this information is not provided by a user beforehand).

Since a model is actually a set of computer data, it is easily possible to extract specific information like geometrical aspects and/or dimensions of the virtually represented object from that data.

The model may include more than one part of an imaged object, with possibly one or more parts not being visible in the X-ray projection image. For example, a model of an implant may include a screw intended to be used with an implant, but only the implant is already introduced into an anatomic structure and thus only the implant is visible in the X-ray projection image.

It is also noted that a model may not be a complete 3D model of a real object, in the sense that it only describes certain geometrical aspects of an object, such as the fact that the femoral head can be approximated by a ball in 3D and a circle in the 2D projection image, or the fact that a pedicle of a vertebra has a cylinder-like shape.

In accordance with an embodiment, a system for processing X-ray images generally comprises a processing unit and a software program product, wherein, when the software program product is executed by the processing unit, the system is caused to perform the following steps. Firstly, an X-ray image is received, wherein the X-ray image is a projection image at least of a first object and a second object. At least the first object and the second object are then classified and a respective 3D model of the objects is received, for example from a database. Directly on the basis of the X-ray image and/or on the basis of the respective 3D model, a first geometrical aspect of the first object is determined and identified in relation to the 3D model of the first object, and a second geometrical aspect of the second object is determined and identified at the 3D model of the second object. The second geometrical aspect may be a point.

Further, a spatial relation between the first object and the second object is determined based on the 3D model of the first object, the 3D model of the second object and the information that the second geometrical aspect, e.g. a point of the second object, is located on the geometrical aspect of the first object. The geometrical aspect of the first object may be a plane, a line or a point. It will be understood that a geometrical aspect may also include a plurality of the mentioned aspects as well as a combination thereof. In consequence, a geometrical aspect as used herein may result in a more complex shape such as an edge of a fragment in case of a fracture.

According to an embodiment, the geometrical aspect of the first object is a plane or a line, and the X-ray image is generated with an imaging direction being inclined relative to the geometrical aspect with an angle in a range between 10 degrees and 65 degrees. In fact, the plane or line associated with the first object may be inclined relative to the imaging direction. An X-ray image generated with such an inclined imaging direction may include enough information about the first object so as to allow the determination of the geometrical aspect. In other words, the appearance of the first object as visible in the X-ray image provides enough information for the processing unit of the system for classifying the object and identifying the geometrical aspect automatically. The range of the angle may also be between 15 degrees and 45 degrees. Alternatively, the angle may be in the range between 20 degrees and 30 degrees. Assuming that the system provides an instruction for a user for the adjustment of the C-arm, the system may instruct the user to orient the imaging direction relative to the geometrical aspect of the first object or it may instruct the user to orient the geometrical aspect of the first object with an angle of for example 25 degrees.

In accordance with a further embodiment, the system is further caused to determine a deviation of the 3D position and 3D orientation of the second object from an intended spatial relation of the second object relative to the first object.

For example, the first object may be an aspect of an anatomy or a first implant and the second object may be a tool or a second implant. As described below in more detail, the first object may be a vertebra and the second object a pedicle screw. Alternatively, the first object may be an intramedullary nail and the second object may be a locking screw for distally locking the nail. Alternatively, the second object may be a drill or a k-wire used to prepare a path for a screw into and through a bone. Alternatively, the first object and the second object may each be bone fragments, which must be anatomically reduced.

According to an embodiment, the selected point of the second object may be a tip of the object, e.g. of a drill, and the information about the 3D location of said tip is a point of contact of the tip with a surface of the first object, e.g. an outer surface of a vertebra or of a long bone like the femur.

According to an embodiment, the system may comprise a device for providing information to a user, wherein the information includes at least one piece of information out of the group consisting of X-ray images and instructions regarding step of a procedure. It will be understood that such a device may be a monitor for visualization of the information or may be a loudspeaker for providing the information acoustically.

According to yet another embodiment, the characteristics of the X-ray imaging device, which is intended to be used together with the described software program product being executed on a processing unit of the system, may be known. It may be that, on the one hand, imaging characteristics may be known and may be taken into account when processing X-ray image data, and may, on the other hand, facilitate instructions to a user for adjustment of the C-arm for imaging on the basis of the known geometry of the imaging device and the possibilities of changing the position and orientation of the C-arm. The C-arm based X-ray imaging device may be part of the system.

The appearance of an object in a projection image may be affected by the X-ray imaging procedure. For example, imaging parameters like the imaging direction (which describes the direction in which the X-ray beam passes through an object, also called "viewing direction") relative to gravity, a zoom, the radiation intensity, and/or a presence of a magnetic field may influence the appearance of an object in a projection image. Those or further imaging parameters may cause characteristic changes in the projection image like deformations of the projected object due to a pillow effect, mechanical bending of a C-arm imaging device depending on the imaging direction, a curvature, noise, and/or distortion. Here, those changes are denoted as image characteristics.

It will be understood that it may be possible to determine those image characteristics with a sufficient precision in a projection image. For example, a position of a structure shown in an edge region of the image may be more affected by a pillow effect than a structure in the center of the image. In consequence, the characteristics of a pillow effect may be determined with a sufficient precision based on a structure of known shape that spans from an edge region to a central region. Image characteristics determined for a region in the 2D X-ray may be extrapolated to the entire image.

The appearance of an object in an X-ray image further depends inter alia on attenuation, absorption, and deflection of X-ray radiation, which depend on the object's material. The more material the X-ray beam must pass through, the less X-ray radiation is received by the X-ray detector. This affects not only the appearance of the object within its outline, but it may also change the shape of the outline itself in the X-ray projection image, in particular in areas where the object is thin. The strength of this effect also depends on the X-ray intensity and the amount of tissue surrounding the object, which the X-ray beam must pass through. The latter depends on the body mass index of the patient and the imaging direction. The amount of soft tissue surrounding the object could be derived from a database, which considers, e.g., ethnicity, gender, body mass index, age.

Taking into account image and object characteristics as well as the effects of X-ray attenuation, absorption, and deflection, a virtual projection of a model may be deformed and/or distorted like the object is deformed and/or distorted in the X-ray projection image. Such a virtual projection may then be matched to the projection seen in the X-ray image. It will be understood that the matching of the object in the X-ray projection image to the model may include an adaptation of image characteristics of the X-ray projection image to image characteristics of the virtual projection of the model and/or an adaptation of image characteristics of the virtual projection of the model to image characteristics of the X-ray projection image. It is also understood that a match in the 3D projection volume, by minimizing distances in 3D, may also be possible.

The physical dimensions of an object are related to the dimensions of its projection in an X-ray image through the intercept theorem (also known as basic proportionality theorem) because the X-ray beams originate from the X-ray source (the focal point) and are detected by an X-ray detector in the image plane. The precise imaging depth (which is the distance of the object from the image plane) is not generally required in the context of this invention. However, if an object is sufficiently large, the imaging depth may be determined through the intercept theorem, and the larger the object, the more precise this determination will be. Yet even for small objects, an approximate estimation of imaging depth may be possible. Alternatively, the imaging depth may also be determined if the size of the X-ray detector and the distance between image plane and focal point are known.

According to an embodiment, a deep neural net (DNN) may be utilized for a classification of an object in an X-ray projection image (e.g., proximal part of femur, distal part of femur, proximal part of nail, or distal part of nail, etc.). It is noted that a DNN may classify an object without determining its position (see, e.g., Krizhevsky, A., Sutskever, I., and Hinton, G. E. ImageNet classification with deep convolutional neural networks. In NIPS, pp. 1106-1114, 2012). It is further noted that an object may also be classified even if it is known which object should be recognizable in the X-ray image. A neural net may also be utilized for a rough classification of the imaging direction (e.g., AP vs. ML, cf. the paper: Aaron Pries, Peter J. Schreier, Artur Lamm, Stefan Pede, Jürgen Schmidt: Deep morphing: Detecting bone structures in fluoroscopic X-ray images with prior knowledge, 2018, available online at https://arxiv.org/abs/1808.04441). Such a classification of object and imaging direction may be used to select an appropriate model for following processing steps. It is noted that classification may done by other means, or by a priori information about which object(s) is or are visible in the image.

According to an embodiment, the outline of the classified object may be detected in the X-ray image. For objects with variable shape such as anatomical structures, this may proceed by using a "deep morphing" approach as described in the above cited paper by Pries et al. (2018). This paper proposes an approach based on a deep neural network to detect bone structures in fluoroscopic X-ray images. The technique specifically addresses the challenges in the automatic processing of fluoroscopic X-rays, namely their low quality and the fact that typically only a small dataset is available for training the neural network. The technique incorporates high-level information about the objects in the form of a statistical shape model. The technique consists of a two-stage approach (called deep morphing), where in the first stage a neural segmentation network detects the contour (outline) of the bone or other object, and then in the second stage a statistical shape model is fit to this contour using a variant of an Active Shape Model algorithm (but other algorithms can be used as well for the second stage). This combination allows the technique to label points on the object contour. For instance, in the segmentation of a femur, the technique will be able to determine which points on the contour in the 2D X-ray projection image correspond to the lesser trochanter region, and which points correspond to the femoral neck region, etc. Objects described by a deterministic model (e.g., a nail) may also be detected by deep morphing, or simply by a neural segmentation network, as in the first stage of deep morphing.

In a further step, taking into account image and/or object characteristics as well as the effects of X-ray attenuation, absorption, and deflection, a virtual projection of the model may then be adjusted to match the appearance of the object in the X-ray projection image. According to an embodiment, for objects described by a deterministic model, this matching may proceed, for example, along the lines described in the paper: Lavallée S., Szeliski R., Brunie L. (1993) Matching 3-D smooth surfaces with their 2-D projections using 3-D distance maps. In: Laugier C. (eds) Geometric Reasoning for Perception and Action. GRPA 1991. Lecture Notes in Computer Science, vol. 708. Springer, Berlin, Heidelberg. In this approach, image characteristics and object characteristics as well as the effects of X-ray attenuation, absorption, and deflection may be accounted for by introducing additional degrees of freedom into the parameter vector or by using a suitably adjusted model.

A neural net may be trained based on a multiplicity of data that is comparable to the data on which it will be applied. In case of an assessment of bone structures in images, a neural net should be trained on the basis of a multiplicity of X-ray images of bones of interest. It will be understood that the neural net may also be trained on the basis of simulated X-ray images. Simulated X-ray images may, for example, be generated from 3D CT data, as described in the appendix of the paper: Aaron Pries, Peter J. Schreier, Artur Lamm, Stefan Pede, Jürgen Schmidt: Deep morphing: Detecting bone structures in fluoroscopic X-ray images with prior knowledge, available online at https://arxiv.org/abs/1808.04441.

According to an embodiment, more than one neural network may be used, wherein each of the neural nets may specifically be trained for a sub-step necessary to achieve a desired solution. For example, a first neural net may be trained to evaluate X-ray image data so as to classify an anatomical structure in the 2D projection image, whereas a second neural net may be trained to detect the location of that structure in the 2D projection image. A third net may be trained to determine the 3D location of that structure with respect to a coordinate system. It is also possible to combine neural networks with other algorithms, including but not limited to, Active Shape Models. It is noted that a neural net may also learn to localize an object or to determine an imaging direction without the need to first detect the outline of the object in the 2D X-ray image. It is also noted that a neural net may also be utilized for other tasks, e.g., a determination of one or more image characteristics like a pillow effect.

According to an embodiment, an object may also be manually classified and/or identified in the X-ray projection image. Such a classification or identification may be supported by the device by automatically referring to structures that were recognized by the device.

According to an embodiment, the system may compute geometrical aspects of an object (e.g., an axis, a plane, a trajectory, an outline, a curvature, a center point, or a one- or two-dimensional manifold), and dimensions of an object (e.g., a length, a radius or a diameter, a distance). This may be accomplished due to the correspondence between the model and the virtual projection that has been matched to the projection seen in the X-ray image.

When displaying the X-ray projection image, geometrical aspects and/or dimensions may be shown as an overlay in the projection image. Alternatively and/or additionally, at least a portion of the model may be shown in the X-ray image, for example as a transparent visualization or 3D rendering, which may facilitate an identification of structural aspects of the model and thus of the imaged object by a user.

The present invention provides for a 3D reconstruction and localization of an object whose shape and appearance have some variability. Such objects may for instance be described by a 3D statistical shape or appearance model. This can be done based on a single X-ray image or multiple X-ray images. Based on one image of an anatomical object, the model may be deformed in such a way that its virtual projection matches the actual projection of the object in the X-ray image. If multiple X-ray images are acquired, the information from them may be fused (registered) to increase the accuracy of 3D reconstruction and/or determination of spatial positions or orientations. The matching of a virtual projection to an actual projection in an X-ray image (e.g., using Deep Morphing) may be performed with higher accuracy if the imaging direction is known or can be determined, or in case of registering multiple X-ray images, the 3D angles (which may, for instance, be represented by Euler angles) between imaging directions are known or can be determined.

According to an embodiment, a determination of the relative 3D positions and 3D orientations between multiple objects is provided, even if localization of at least one of the objects individually would not be possible with sufficient accuracy. This may be addressed by utilizing geometric a priori information about the relative 3D position and/or 3D orientation between at least two objects/structures in the X-ray image. This may, for instance, be the information that a point of one object lies on a line whose relative 3D position and orientation with respect to another object is known. Another example would be that the relative 3D position and 3D orientation between a geometrical aspect of one anatomical object and a geometrical aspect of another anatomical object are known. Because there may still be remaining ambiguities, it may also be necessary to restrict the X-ray imaging direction to (i) a particular anatomically relevant view (e.g., true ML) or to (ii) an angle range allowing one of the objects being viewed from a particular direction.

It is noted that a processing unit may be realized by only one processor performing all the steps of the process, or by a group or a plurality of processors, which need not be located at the same place. For example, cloud computing allows a processor to be placed anywhere. For example, a processing unit may be divided into (i) a first sub-processor on which a first neural net is implemented assessing the image data including a classification of anatomical structures like a bone surface, (ii) a second sub-processor on which a second neural net is implemented specialized for determining an imaging direction of the classified anatomical structure, and (iii) a further processor for controlling a monitor for visualizing results, or a loudspeaker for providing instructions to the user acoustically. One of these or a further processor may also control movements of, for example, a C-arm of an X-ray imaging device.

According to an embodiment, the device may further comprise storage means providing a database for storing, for example, X-ray images. It will be understood, that such storage means may also be provided in a network to which the system may be connected, and that data related to the neural net may be received over that network.

Furthermore, the device may comprise an imaging unit for generating at least one 2D X-ray image, wherein the imaging unit may be capable of generating images from different directions.

The device may further comprise input means for manually determining or selecting a position or part of an object in the X-ray image, such as a bone outline, for example for measuring a distance in the image. Such input means may be for example a computer keyboard, a computer mouse or a touch screen, to control a pointing device like a cursor on a monitor screen, which may also be included in the device.

It is noted that all references to C-arm movements or rotations in this patent application always refer to a relative repositioning between C-arm and patient. Hence, any C-arm movement or rotation may in general be replaced by a corresponding movement or rotation of the patient/OR table, or a combination of C-arm movement/rotation and patient/table movement/rotation. This may be particularly relevant when dealing with extremities since in practice moving the patient's extremities may be easier than moving the C-arm. It is noted that the required patient movements/rotations are generally different from the C-arm movements/rotations, in particular, typically no translation of the patient is necessary if the target structure is already at the desired position in the X-ray image. The system may compute C-arm adjustments and/or patient adjustments.

The methods and techniques disclosed in this application may be used in a system that supports a human user or surgeon, or they may also be used in a system where some or all of the steps are performed by a robot. Hence, all references to a "user" or "surgeon" in this patent application may refer to a human user as well as a robotic surgeon, a mechanical support device, or a similar apparatus. Similarly, whenever it is mentioned that instructions are given how to adjust the C-arm, it is understood that such adjustments may also be performed without human intervention, i.e., automatically, by a robotic C-arm, or they may be performed by OR staff with some automatic support. It is noted that because a robotic surgeon and/or a robotic C-arm may operate with higher accuracy than humans, iterative procedures may require fewer iterations, and more complicated instructions (e.g., combining multiple iteration steps) may be executed.

A computer program product may preferably be loaded into the random-access memory of a data processor. The data processor or processing unit of a system according to an embodiment may thus be equipped to carry out at least a part of the described process. Further, the invention relates to a computer-readable medium such as a CD-ROM on which the disclosed computer program may be stored. However, the computer program may also be presented over a network like the World Wide Web and can be downloaded into the random-access memory of the data processor from such a network. Furthermore, the computer program may also be executed on a cloud-based processor, with results presented over the network.

It is noted that prior information about an implant (e.g., the size and type of a nail) may be obtained by simply scanning the implant's packaging (e.g., the barcode) or any writing on the implant itself, before or during surgery.

For a further understanding of the invention, an exemplary method is described, of inserting a bone screw into a long bone and through a hole in a bone nail for distal locking of the bone nail being in said long bone. The hole has a hole axis which may be considered the geometrical aspect of the nail. The method may comprise the steps of arranging a drill with its tip being in contact with an outer surface of the long bone so that the tip of the drill is positioned on the hole axis of the hole in the bone nail, wherein a drill axis of the drill is oriented with an angle of 10 to 70 degrees relative to the hole axis. Here, the hole axis is a line as geometrical aspect of the first object, i.e. the bone nail and the tip of the drill is the point as geometrical aspect of the second object, i.e. the drill.

With the tip of the drill on the outer surface of the long bone, a first X-ray image of the bone drill and the bone nail within the long bone is generated, with an imaging direction being in the direction of the hole axis in the bone nail. A person skilled in the art will understand that the imaging direction may be a true mediolateral direction and the hole should thus be visible as a circle, in case of distal locking of a femur nail.

The system may then determine an actual angle between the drill axis and the hole axis based on the knowledge of the contact point, based on a 3D model of the drill and based on a 3D model of the bone nail. Based on the determined angle, the system may give instructions to change the orientation of the bone drill so that the tip is still on the bore axis and the drill axis is close to the hole axis. Here, "close" means with a deviation of up to 15 degrees from the hole axis. It may also suffice to approximately align the drilling trajectory with the imaging direction.

While maintaining the position of the drill tip, a second X-ray image of the drill and the bone nail within the long bone may be generated, with a second imaging direction being oriented relative to the first imaging direction with an angle in the range between 10 and 65 degrees. An easy way of changing the orientation may be, when starting from a mediolateral imaging direction, to move only the C-arc in a direction to anterior-posterior. Also here, it is decisive that the drill, i.e. the second object, is sufficiently visible in the next X-ray image so as to allow an automatic determination of e.g. position and orientation of the drill axis. The angle may thus be in the range between 10 and 65 degrees, preferably between 15 and 45 degrees and most preferably between 20 and 30 degrees.

Based on the second X-ray image, a deviation of the 3D position and 3D orientation of the drill axis from the hole axis of the hole in the bone nail may be determined. In case of a deviation, the position and orientation of the bone drill may be adjusted, and a bore may be drilled into the long bone and through the hole in the bone nail. With the same angle of the imaging direction relative to the drill axis, drilling along the target trajectory may be checked by one or more X-ray images.

The principles of the invention may also be applied to a method of inserting a bone screw into a pedicle of a vertebra. The method may comprise the steps of arranging a drill with its tip being in contact with an outer surface of the vertebra so that the tip of the drill is positioned on an axis extending through a pedicle of the vertebra, wherein a drill axis of the drill is oriented with an angle of 10 to 65 degrees relative to the target axis through the pedicle.

Like in the above described method, a first X-ray image is generated, the image including the drill and the vertebra, from an imaging direction, e.g., true AP, such that the opening of the pedicle is clearly visible. A difference between the two methods may be seen in that the imaging direction of that first X-ray image may be considered as an anterior-posterior direction, with the patient lying flat on his/her chest, and that the imaging direction need not be in line with the pedicle axis (target trajectory) because both objects touch each other. With such an inclined view, and based on the knowledge of the contact point, the relative 3D position and 3D orientation between the drill and the pedicle may be determined.

As a next step, an actual angle between the drill axis and the axis through the pedicle may be determined, based on a 3D model of the drill and based on a 3D model of the vertebra. Following instructions which may be provided by the system, the orientation of the drill may be changed so that the tip of the drill is still on the axis through the pedicle and the drill axis is close to the target axis through the pedicle. A second X-ray image from possibly the same direction may be generated in case the inclination of the pedicle axis to the viewing direction is large enough so that neither power tool nor hand are occluding the view. Typically, the inclination between the pedicle axis and the true AP viewing direction onto the corresponding vertebra is 10 to 45 degrees. If necessary, the position and orientation of the drill may be adjusted, followed by drilling into the vertebra and through the pedicle.

The principles of the invention may also be applied to a method of inserting a bone screw into a sacroiliac (SI) joint. The method may comprise the steps of arranging a drill with its distal tip being in contact with an outer surface of the vertebra so that the tip of the drill is positioned on an axis extending through the desired drilling canal through the SI joint wherein a drill axis of the drill is oriented with an angle of 10 to 65 degrees relative to the target axis through the pedicle.

Like in the above described method, a first X-ray image is generated, the image including the relevant parts of the drill, the ilium and the sacrum, with an imaging direction being in line with the direction of the drilling canal. As a next step, an actual angle between the drill axis and the axis through the drilling canal may be determined, based on the knowledge of the contact point, based on a 3D model of the drill and based on a 3D model of the vertebra. Following instructions which may be provided by the system, the orientation of the drill may be changed so that the tip of the drill is still on the axis of the drilling canal and the drill axis is close to the target axis of the drilling canal.

A second X-ray image of the drill, the relevant part of the ilium and the relevant part of the sacrum is then generated, with interchanged orientations of the drill and the imaging direction. The drill may now be more or less on the target trajectory through the drilling canal and a second imaging direction may be oriented relative to the first imaging direction with an angle in the range between 10 and 65 degrees. The C-arc of the X-ray imaging device may be rotated to an inclined viewing direction. The range of the angle between the two imaging directions may also be between 15 and 40 degrees. Alternative, the range may be between 20 and 30 degrees. With such an inclined view, a deviation of the 3D position and 3D orientation of the drill axis from the target axis through the drilling canal may be determined. If necessary, the position and orientation of the drill may be adjusted, followed by drilling into the ilium and the SI joint.

As should be clear from the above description, a main aspect of the invention is a processing of X-ray image data, allowing an automatic interpretation of visible objects. The methods described herein are to be understood as methods assisting in a surgical treatment of a patient. Consequently, the method may not include any step of treatment of an animal or human body by surgery, in accordance with an embodiment.

It has to be noted that embodiments are described with reference to different subject-matters. In particular, some embodiments are described with reference to method-type claims (computer program) whereas other embodiments are described with reference to apparatus-type claims (system/ device). However, a person skilled in the art will gather from the above and the following description that, unless otherwise specified, any combination of features belonging to one type of subject-matter as well as any combination between features relating to different subject-matters is considered to be disclosed with this application.

The aspects defined above and further aspects, features and advantages of the present invention can also be derived from the examples of the embodiments to be described hereinafter and are explained with reference to examples of embodiments also shown in the figures, but to which the invention is not limited.

Figure 1:
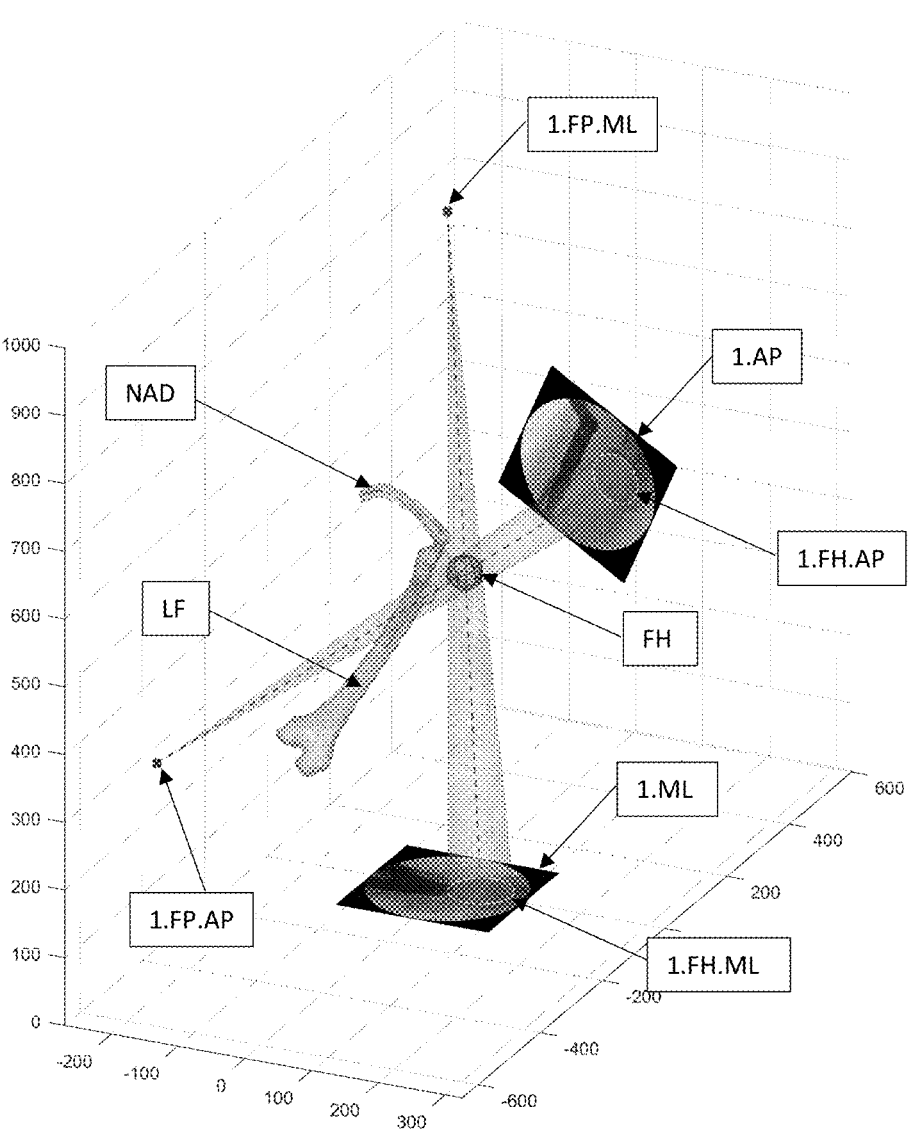
FIG. 1 shows an example for a 3D registration of AP and ML images.

Throughout the drawings, the same reference numerals and characters, unless otherwise stated, are used to denote like features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF THE EMBODIMENTS

The following detailed description is merely exemplary in nature and is not intended to limit the invention or the application and uses of the invention. Furthermore, there is no intention to be bound by any theory presented in the preceding background of the invention or the following detailed description.

3D Reconstruction and Localization of an Anatomical Object Based on One X-Ray Image The above cited paper on Deep Morphing by Pries et al. (2018) proposes a method that enables a system to detect (in a 2D projection image) the outline/contour of a bone and label points on the contour. For instance, in the segmentation of a femur, the technique is able to determine which points on the contour in the 2D X-ray projection image correspond to the lesser trochanter, and which points correspond to the femoral neck, etc. Given a 3D statistical shape or appearance model of the same anatomical structure, this model can then be deformed in a way that its virtual projection matches the actual projection in the X-ray image, hence leading to a 3D reconstruction of the anatomical structure and allowing a localization of the object and determination of the imaging direction. On the other hand, if the imaging direction is already known, a 3D reconstruction of the anatomical object may be performed with higher accuracy. The imaging direction may be known, for instance, because the surgeon was instructed to acquire an X-ray in a specific direction (e.g., true AP or true ML), or because a specific imaging direction was detected by an algorithm, e.g., by the invention by Blau filed as patent application on 23 Aug. 2018.

The accuracy of the 3D reconstruction of an anatomical object may be improved upon by using a priori information. This a priori information may be the size or the gender of the patient, but also more anatomy-specific information like geometric information about the anatomical object to be reconstructed. For the example of a 3D reconstruction of a proximal femur based on an ML image, this information may include the length of the femoral neck or the CCD angle. However, because such information may not be determined with sufficient precision in typical ML images, it may be extracted from AP images that are routinely acquired earlier in the course of the surgery on the proximal femur. The more information is used from earlier images, the more accurate a 3D reconstruction may be. Another way of describing this procedure would be to say that, based on an AP image, a 3D reconstruction of the proximal femur may be performed with typical remaining uncertainties (such as the width of the femoral neck in AP direction), and this 3D reconstruction serves as a priori information or as a starting point for the 3D reconstruction based on a later ML image.

Geometric a priori information may also consist of a known correspondence between a point in the 2D projection image and a point in the 3D model of the anatomical object. Less specific geometric information may still be helpful, e.g., if it is known that:

a point in the 2D projection image corresponds to a point on a line whose position and orientation with respect to the 3D model of the anatomical object is known; or a point in the 2D projection image corresponds to a point on a plane whose position and orientation with respect to the 3D model of the anatomical object is known.

Such geometric a priori information may be provided by user input, for instance on a user interface, or by the surgeon placing an object (e.g., a tool such as a drill or a k-wire) on a specific anatomical point visible in the 2D projection image. This may be achieved for prominent anatomical features, possibly in specific imaging directions (e.g., true AP or true ML), or by palpating or visual identification on the actual object. All of this a priori information significantly reduces ambiguities in the 3D reconstruction.

Determination of Relative 3D Position and 3D Orientation Between Objects by Reducing or Resolving Ambiguities It is discussed in the invention by Blau filed as patent application on 26 Nov. 2018 how the relative 3D position and 3D orientation between two objects may be determined if both objects can be localized based on a 2D X-ray image and it is known that the two objects are in contact with each other in physical 3D space.

It is proposed in the present invention how to determine the relative 3D position and 3D orientation between two (or more) objects (or structures) based on a 2D X-ray image, if at least one object may not be localized with sufficient accuracy. Such a determination of relative 3D position and 3D orientation may be possible based on a priori information about the 3D position of a specific point of one of the objects relative to another object, which may be obtained, e.g., from a previously acquired X-ray from a specific imaging direction allowing a localization of at least one structure of the other object. In order for this to work, it may also be necessary to restrict the allowable range of imaging directions in the current image.

Figure 8:
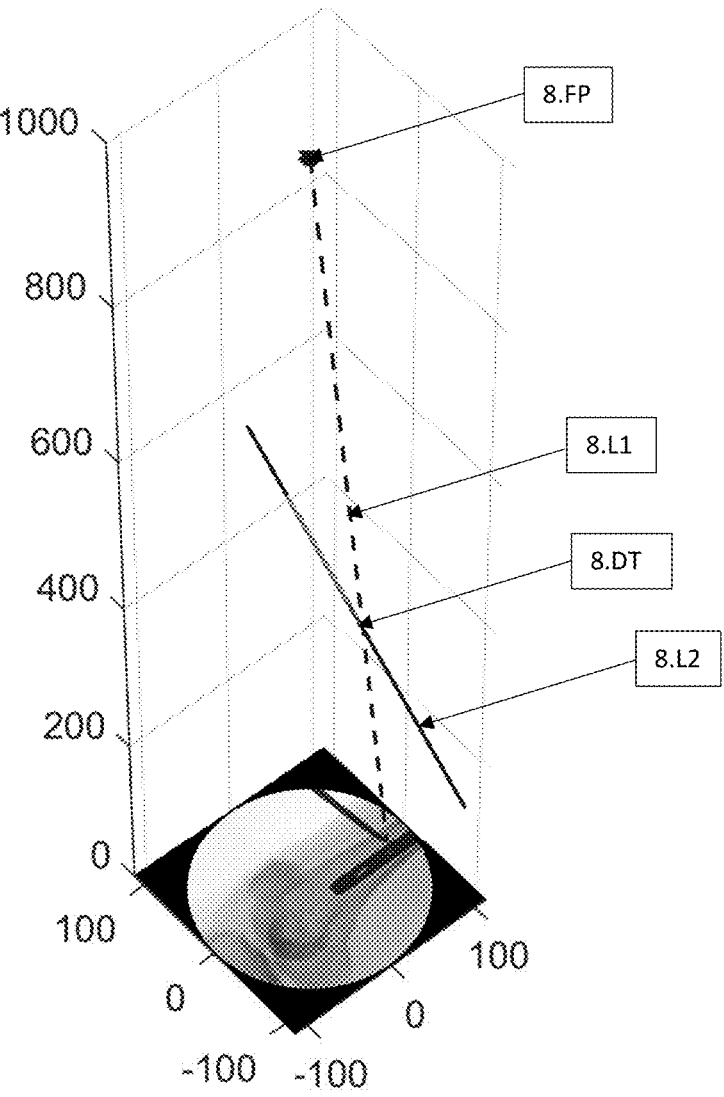
FIG. 8 shows the definition of the drill's tilt.

For the sake of illustration, this will now be explained assuming that one of these objects is a drill and the other object is a nail or some anatomical object (e.g., a vertebra). An anatomical object may be described either using a deterministic 3D model (for the specific patient, generated for instance using a 3D imaging method) or statistical 3D model describing general bone variability. The former case may lead to higher accuracy. Localizing a drill may not always be possible with sufficient accuracy even if a complete and accurate 3D model of the drill is available. As explained above, when localizing an object there is a remaining uncertainty in the imaging depth (the distance of an object from the image plane). This uncertainty in imaging depth in the determination of the drill tip's 3D position also leads to ambiguities concerning the drill's tilt in the direction of imaging depth. As shown in FIG. 8, the drill's tilt is defined as the viewing angle onto the drill's tip, denoted by 8.DT. Since the drill is a very thin and straight structure, with a clearly defined axis, the drill's tilt may be defined as the angle between the dashed line denoted 8.L1, which connects the drill's tip 8.DT and the X-ray focal point 8.FP, and the solid line denoted 8.L2, which is the drill axis.

Figure 9:
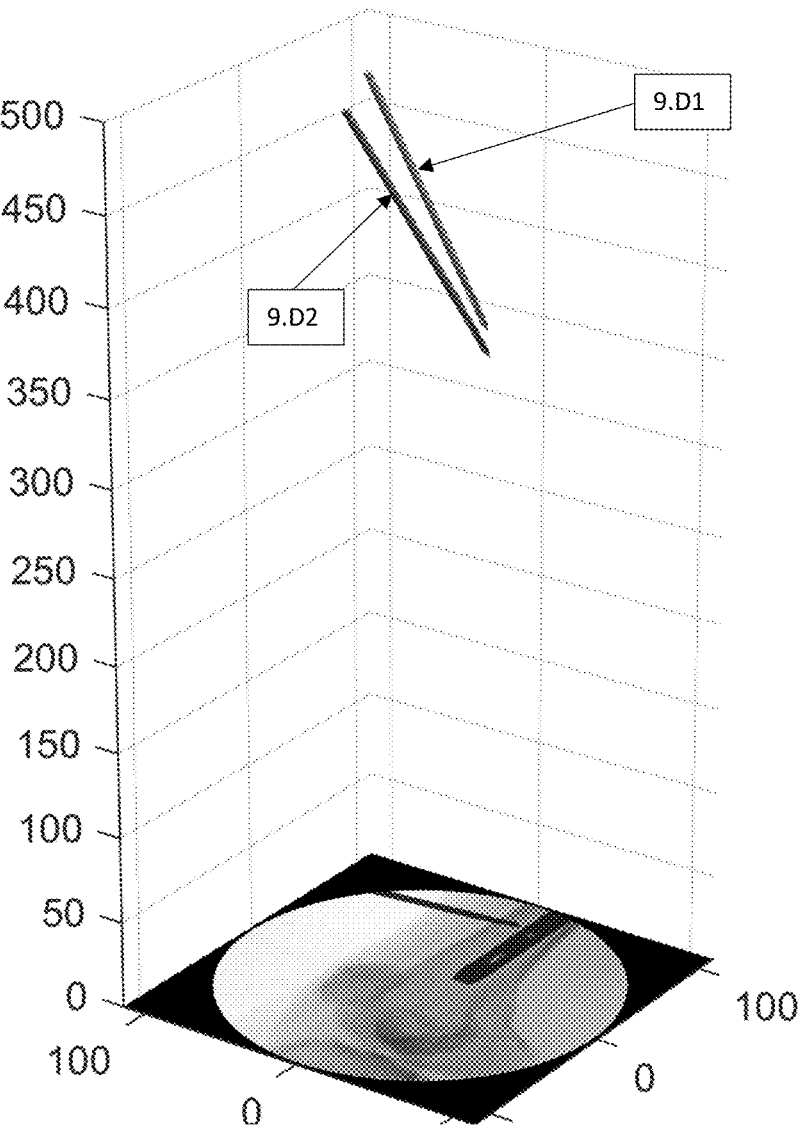
FIG. 9 shows a 3D constellation with two different drill positions.
Figure 10:
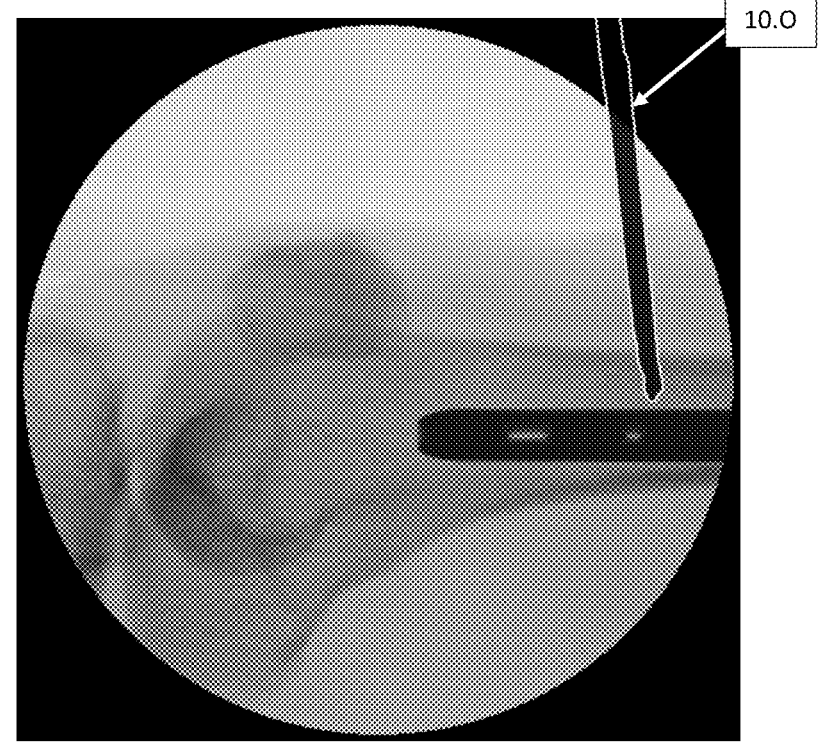
FIG. 10 shows the outline of the drill in an X-ray projection image corresponding to the 3D constellation in FIG. 9.

Consider, for instance, the 3D constellations with two different 3D drill positions (denoted 9.D1 and 9.D2) shown in FIG. 9. The two drill positions differ in imaging depth and also in the drill's tilt (by 6.5 degrees). Yet in an X-ray projection image, the two drill positions may not be distinguishable as they lead essentially to the same X-ray projection, as shown by the more or less identical drill outline 10.O in FIG. 10.

There are two main reasons for this:

1. The drill is a comparatively thin instrument of more or less constant diameter, which in a typical X-ray image is only a few pixels wide. In the X-ray projection, an object tilted in imaging direction is depicted wider on one end and smaller on the other. This, however, may only be detectable if this change in width is sufficiently strong (e.g., at least one pixel wide). For a required accuracy in angle detection of, e.g., less than 3 degrees with a thin drill of, e.g., less than 4 mm diameter, this may not generally be the case.

Localizing an instrument such as a drill (with diameter of a few mm), of which only the front part is visible in the X-ray, from a viewing angle (which is the drill's tilt) close to 90 degrees may not generally be possible with sufficient accuracy because the sine function of small angles has a slope close to zero. For instance, at an angle of 70 degrees, the drill's projection is only shortened by 6 percent, which leads to an insignificant change in the drill tip's projected shape. Such a small change may not be sufficient to determine the drill's tilt with an accuracy of approx. 3 degrees. The limit of detectability is a tilt of approximately 65 degrees, where the drill's projection is shortened by 9.4 percent. Depending on the tool, this may or may not be sufficient for the required accuracy.

Figure 11:
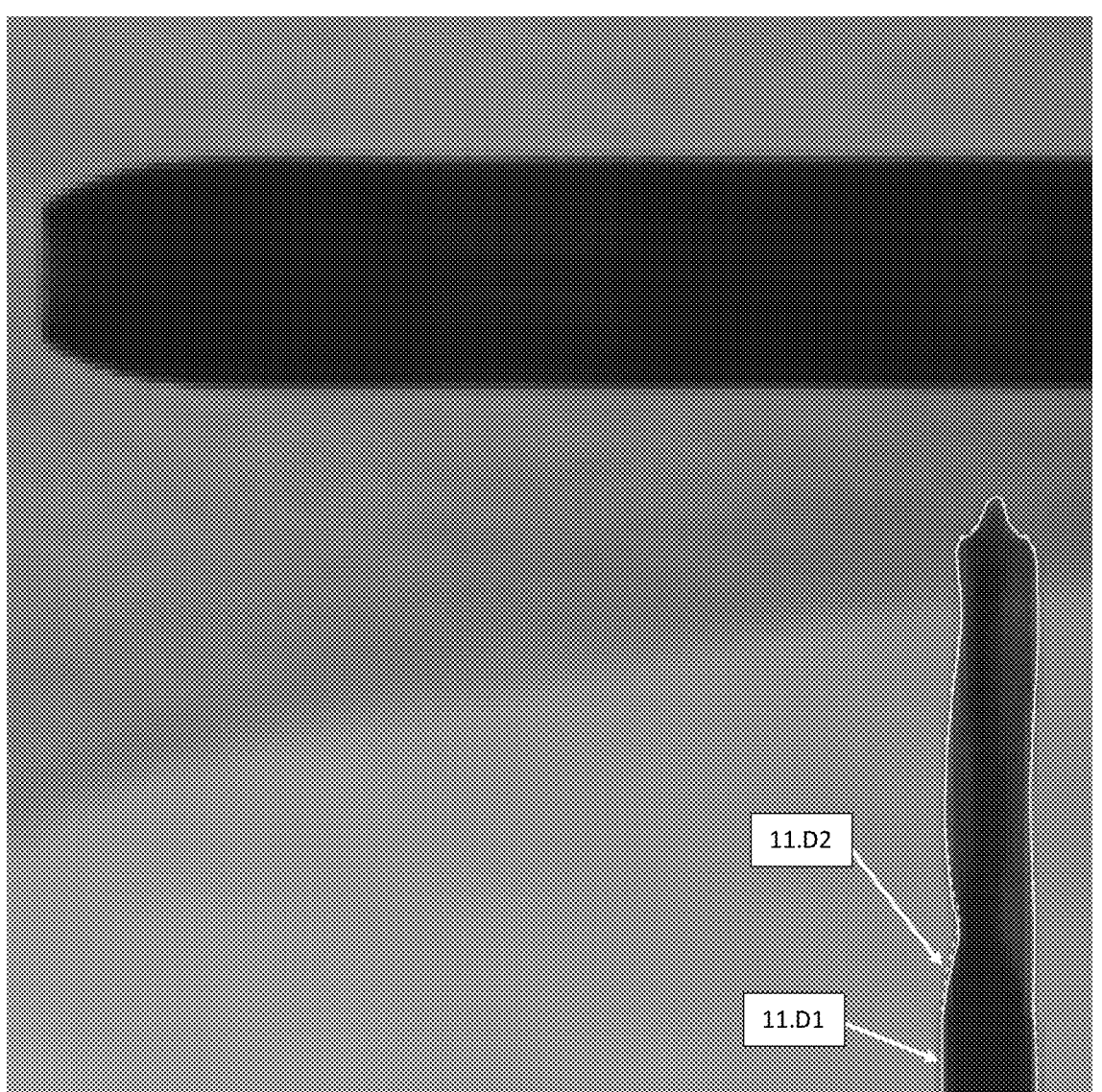
FIG. 11 shows a zoom into an X-ray image, depicting the outlines of two drills corresponding to different tilts (43 and 45 degrees).
Figure 12:
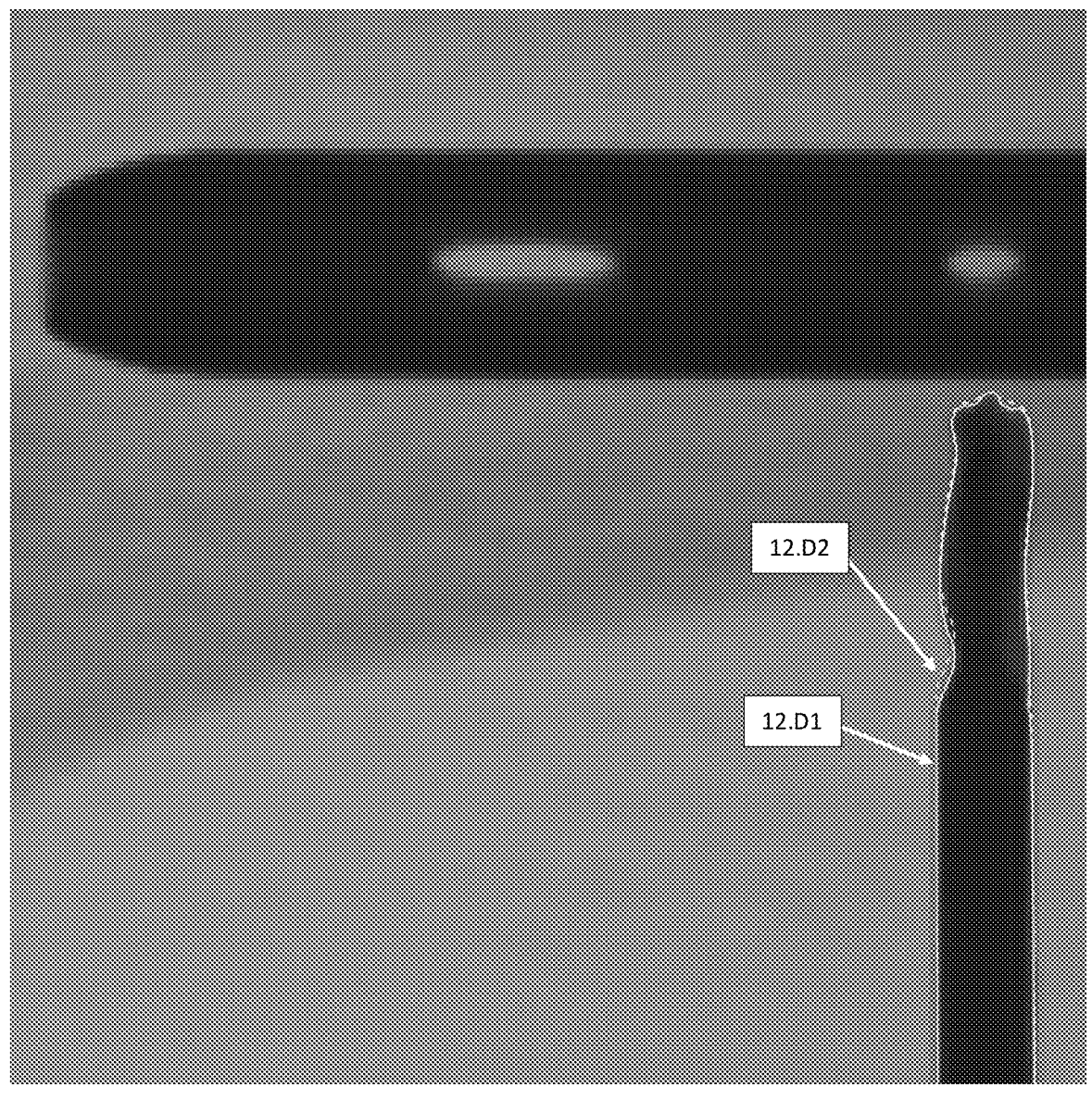
FIG. 12 shows a zoom into an X-ray image, depicting the outlines of two drills corresponding to different tilts (23 and 25 degrees).

The smaller the viewing angle (tilt) is, the easier it becomes to distinguish a difference in tilt of, say, 2 degrees. This is shown in the X-ray image in FIG. 11, which depicts the projections and outlines of two drills: The white solid line labeled as 11.D1 corresponds to a drill with tilt of 45 degrees, and the white dashed line labeled as 11.D2 corresponds to a drill with tilt of 43 degrees. Since these outlines differ in some places, they may be distinguished by the system. Smaller viewing angles lead to more clearly distinguishable outlines. This may be observed in the X-ray image in FIG. 12 showing the projections and outlines of two drills: The white solid line labeled as 12.D1 corresponds to a drill with tilt of 25 degrees, and the white dashed line labeled as 12.D2 corresponds to a drill with tilt of 23 degrees. These outlines now differ clearly in some places, and hence may be easily distinguished by the system.

2. In a typical X-ray image, only the tip and upper part of the drill is visible, but not the other end of the drill. If both ends were visible, the drill's tilt could be determined with high accuracy based on the drill's shortened length in the projection image. This would also be possible if a drill had a marking clearly visible in the X-ray, e.g., half-way along the shaft. While making such a drill would be easy, it would also mean a change in existing tools. Another option would be to use the start of the drill's thread as such a marking. However, with common drills, the beginning of the thread may not be sufficiently clearly visible in the X-ray projection image, and hence it may not generally be possible to use it for this purpose.

The problem may be addressed by a more precise determination of the drill tip's imaging depth, which sufficiently reduces or even resolves ambiguities. This may be possible when determining the relative 3D position and 3D orientation between two objects in an X-ray image. The other object shall be called target object and could, for instance, be a nail. The ambiguity in the drill tip's position relative to the target object may be reduced, for instance, by defining a trajectory whose 3D position and 3D orientation relative to the target object is known, provided that the drill tip's position lies on this trajectory and the imaging direction onto the trajectory at the drill tip's position is sufficiently large (in other words, the trajectory must differ sufficiently from a parallel to the line connecting the drill tip and X-ray focal point).

It may be even more helpful if the 3D position of the drill tip relative to a point on the target object is known. This is the case, for instance, if the drill tip touches the target object, e.g., in sacroiliac screw fixation, where the drill tip touches the ilium. However, it may still be sufficient if it is known that the drill tip lies on a plane whose 3D position and 3D orientation relative to the target object is known. This is the case, for instance, in distal locking of a further hole after completing locking of the first hole. Here, 2 degrees of freedom (DoF) are not determined. For a more detailed description of the distal locking procedure for a nail, see the corresponding section further below.

Moreover, there may also be ambiguities concerning the target object, especially if the target object is an anatomical object. However, if an instrument touches a target object, there are imaging directions where the ambiguities in localizing each of the objects concern different directions. Hence, even in such a case, a sufficiently accurate determination of relative 3D position and 3D orientation may be possible.

In the following, these ideas are now illustrated for a drill touching the trochanter of a proximal femur. In this imaging direction, it may be clearly defined at which point the drill tip touches the femur, e.g., by palpation. Due to ambiguities, as explained above, there are several possibilities for the 3D position and 3D orientation of the drill relative to the femur that would all lead to the same projection of the drill in the X-ray image, but each corresponding to different relative 3D positions and 3D orientations of the depicted anatomy. Selecting which one of these possibilities is the correct one may be possible by jointly considering the depicted anatomy and using the a priori information about the touching point.

Figure 13:
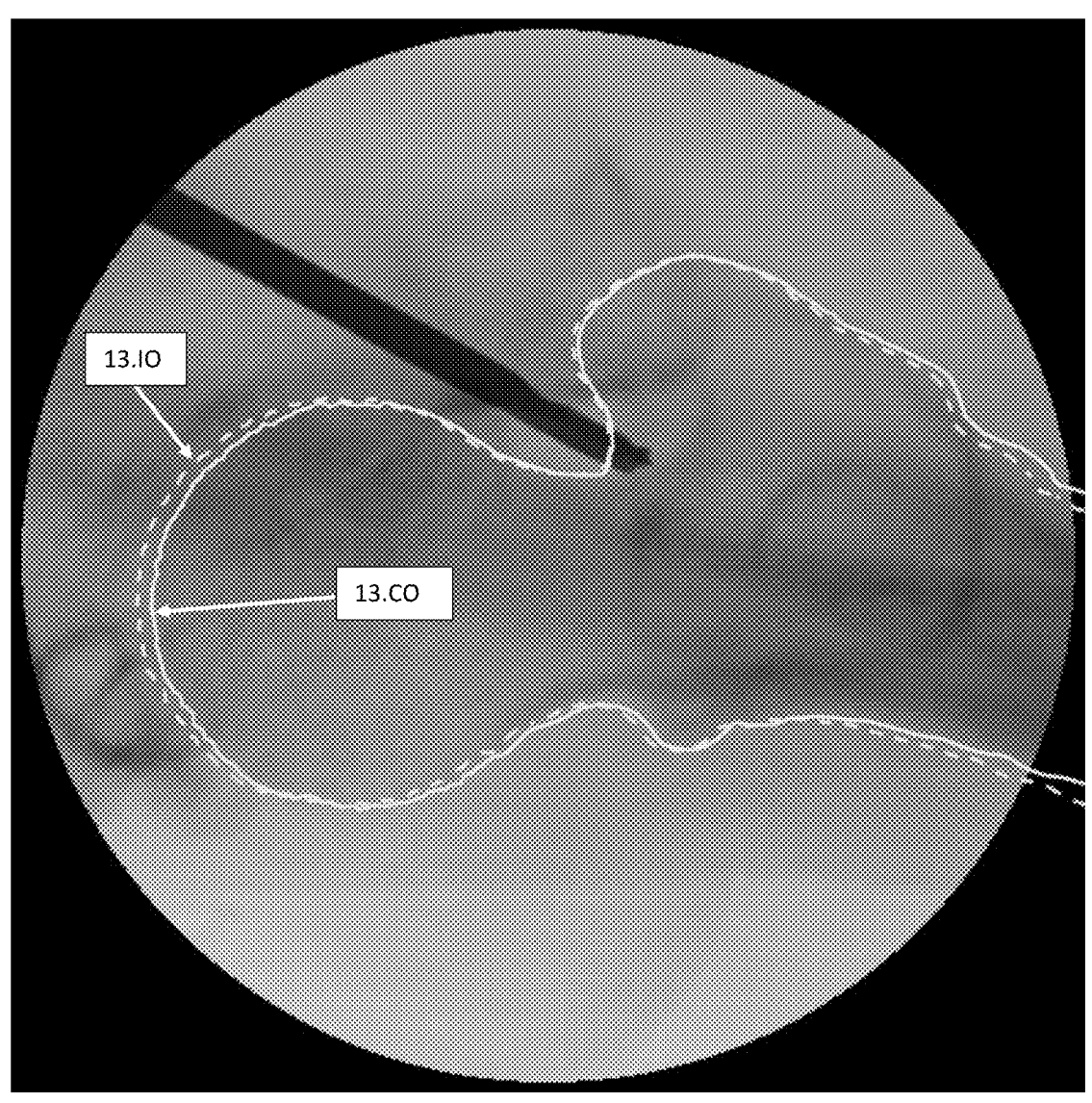
FIG. 13 shows correct and incorrectly determined outlines of a proximal femur, the latter corresponding to an angle error of 2.5 degrees.
Figure 14:
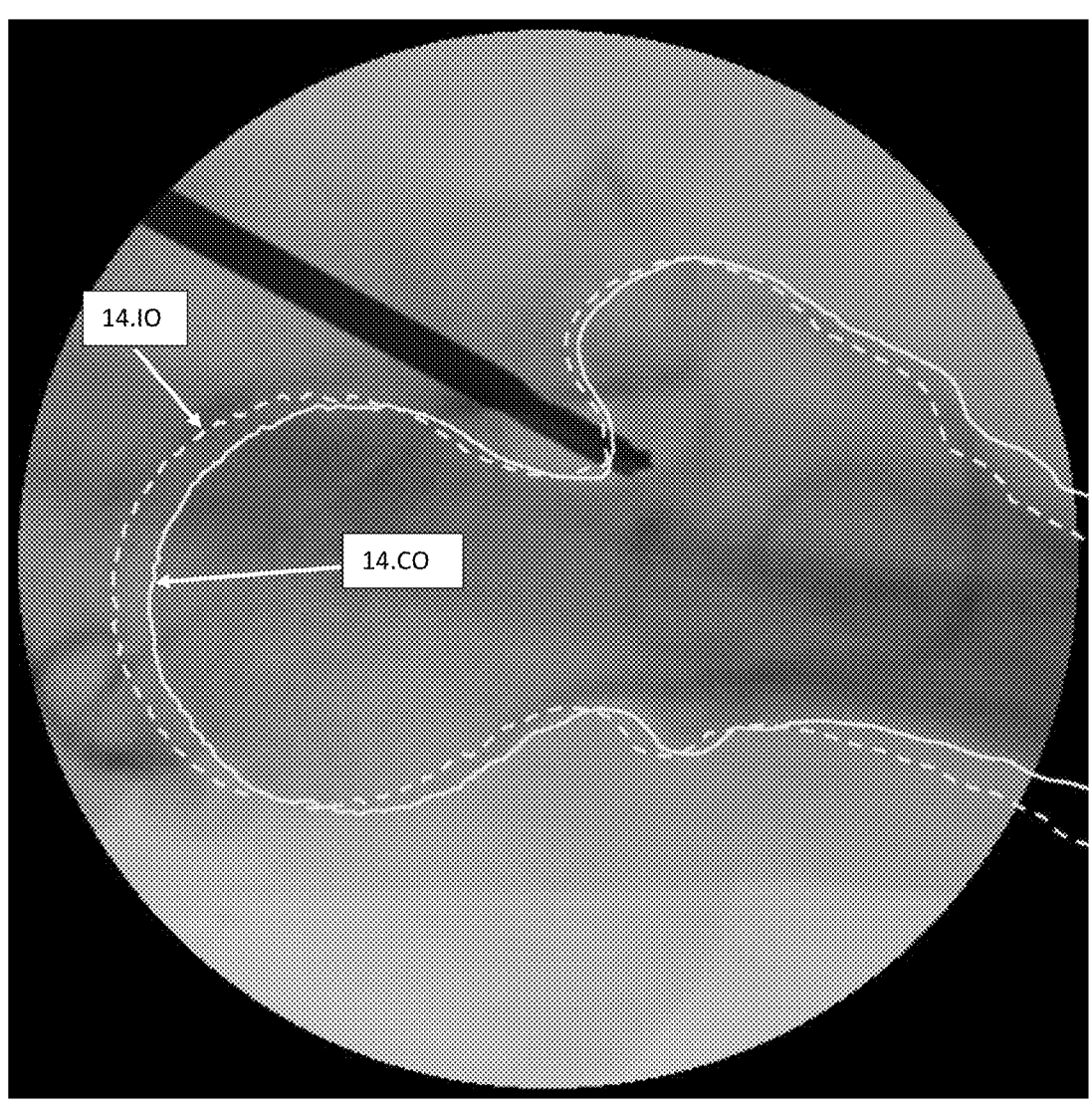
FIG. 14 shows correct and incorrectly determined outlines of a proximal femur, the latter corresponding to an angle error of 6 degrees.

FIG. 13 shows an X-ray image of such a scenario. The white solid line (denoted by 13.CO) is the outline of the femur corresponding to the correct 3D position and 3D orientation of the femur, and the white dashed line (denoted by 13.IO) is the outline of the femur corresponding to one of the incorrect possibilities for 3D position and 3D orientation of the femur. By comparing these possible outlines with the segmented and labeled femur in the X-ray image (which may be achieved, e.g., by Deep Morphing), the one matching the segmented femur best will be selected. In the depicted scenario, the incorrect outline 13.IO clearly differs from the correct outline 13.CO and may thus be discarded even though the incorrect outline only corresponds to an angle error (for the drill's tilt) of 2.5 degrees. Larger angle errors may lead to even more clearly incorrect outlines, as depicted in FIG. 14, where the incorrect outline 14.IO corresponds to an angle error (for the drill's tilt) of 6 degrees and is clearly differentiable from the correct outline 14.CO.

Figure 15:
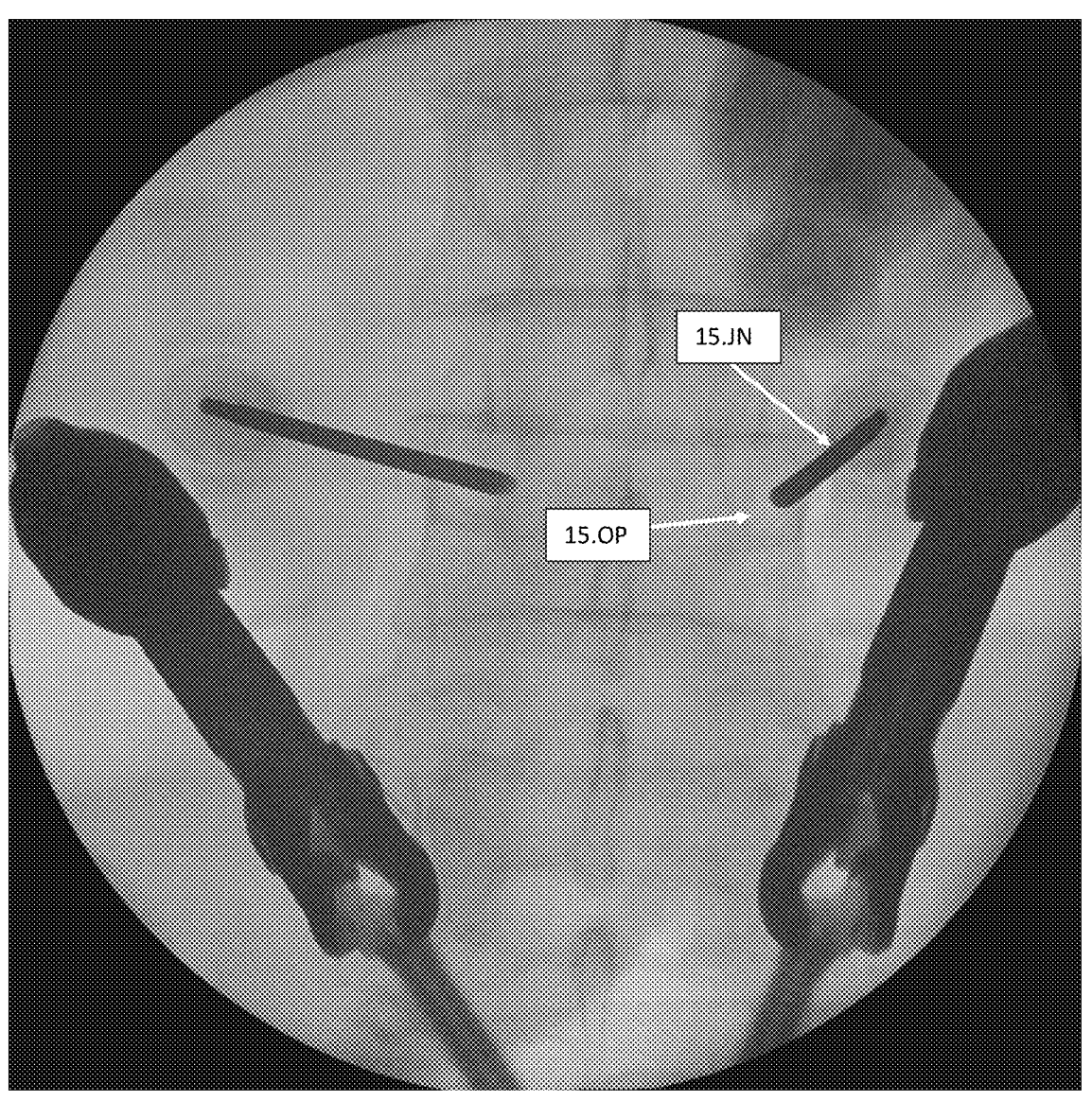
FIG. 15 shows an AP X-ray of a lumbar spine.

A further example may be a determination of the relative 3D position and 3D orientation of a tool with respect to the pedicle of a vertebra. FIG. 15 shows an AP X-ray of a lumbar spine, where the surgeon has placed a Jamshidi Needle (labeled by 15.JN) in the right pedicle of a lumbar vertebra. The opening of the pedicle (labeled by 15.OP) is clearly visible in this specific imaging direction as a brighter area. The center of the pedicle may therefore be identified clearly, and for opening the tool may be placed on this center (pedicle axis). Based on the a priori information that the tool has been placed on the pedicle axis, touching the bone surface, and following the methods outlined above, the relative 3D position and 3D orientation between the tool and the pedicle may be determined for many other imaging directions within a suitable range of angles.

Registration Process of Two or More X-Ray Images from Different Directions

Depending on the bone shape there may still be a remaining ambiguity or matching error in the 3D reconstruction based on one image only. This may be alleviated by acquiring multiple images, potentially from different viewing directions, by rotating and/or translating the C-arm between images. In general, additional images from different imaging directions are more helpful, and the more different the imaging directions are (e.g., AP and ML images), the more helpful additional images may be in terms of a determination of 3D information. However, even adding images from only slightly different viewing angles, which may be more easily acquired during surgery instead of changing to completely different view (AP to ML or vice versa), may be beneficial.

The invention also allows to register multiple X-ray images of at least one common object taken from different directions. This is important because 3D registration allows a determination of relative 3D positions between multiple objects without an explicit determination of the imaging depth.

For the 3D reconstruction of an object of variable shape (typically an anatomical structure described, e.g., by a statistical shape or appearance model and called "Object F" in this section) based on two or more X-ray images, the procedure outlined above for one image may be extended to two or more images. That is, Deep Morphing may be used to detect the contour of Object F and label points on its contour in each 2D X-ray image. Given a 3D statistical shape model of Object F, this model can then be deformed in a way that its virtual projections simultaneously match the actual projections of Object F in two or more X-ray images as closely as possible. This procedure does not need a priori information about the imaging directions because it implicitly determines the imaging direction for each X-ray image.

As an alternative for the registration of a pair of X-ray images taken from two different imaging directions, it may be possible to increase the accuracy of the registration process by taking into account the 3D angle between the imaging directions, which may be determined using two different procedures. The more precisely this angle can be determined, the more precise the 3D registration may be.

One way of determining this angle would be to determine the imaging directions, for instance, using the invention by Blau filed as patent application on 23 Aug. 2018 for each X-ray image and to compute their difference. Another way may be to utilize another object in the X-ray image (called "Object G") whose model is deterministic (e.g., a nail, possibly connected to an aiming device, or an instrument). By matching the virtual projection of Object G to its actual projection in each X-ray image, Object G may be localized. It is noted that, without additional conditions or a priori information, some objects, in particular, a tool such as a drill or k-wire, may not generally have sufficient geometric structure or size to be localized. However, even in such a case, it may be possible to localize Object G with sufficient accuracy provided that (i) the Object G is viewed at a particular angle range in all images to be registered, and (ii) some prior information about the relative 3D position between Objects F and G is available. The prior information in (ii) may in particular be:

- (a) the relative 3D position of a point of Object G and a point of Object F is known; or
- (b) a point of Object G lies on a line in physical 3D space whose relative 3D position and 3D orientation with respect to Object F is known; or
- (c) a point of Object G lies on a plane in physical 3D space whose relative 3D position and 3D orientation with respect to Object F is known.

However, the relative 3D position and 3D orientation between Objects F and G should be identical in both X-ray images, i.e., with as little movement as possible between the objects.

In general, two (or more) images may be registered if they contain an object that is localizable with sufficient accuracy. If the images contain two (or more) objects that do not move relative to each other in between acquiring the images, the image registration may be performed with increased accuracy. An example where this procedure may be employed is the situation where an implant (e.g., a nail) has already been inserted into the bone, and a 3D model (e.g., statistical shape model) of the bone is available. If, in such a scenario, a drill is visible in all images but with different orientations, and its tip (also visible in all images) remains on the same point (e.g., a point on the bone surface), the 3D position of the drill's tip may be determined relative to either of the two objects. This means, in a first image the instrument may be placed on an arbitrary point and in a second image (obtained from a different viewing direction) the instrument's orientation may have changed (e.g., by aiming approximately at the target trajectory) but the instrument's tip remains on the same position. Based on a localization of the target object/ structure (e.g., the nail/nail hole), both images may be registered, which may allow a determination of the 3D position of the point (the instrument's tip) relative to the target object. This point may then be used to determine, with sufficient accuracy, the relative 3D position and 3D orientation between tool and target object/structure.

In other words, a system may be caused by a software program product executed on a processing unit of the system, to receive a first X-ray image, wherein the first X-ray image is a projection image of at least one object, to classify the at least one object and to determine at least one point in the first X-ray image. Then, the system may be caused to receive a second X-ray image, wherein the second X-ray image is a projection image generated with an imaging direction which differs from the imaging direction utilized to generate the first X-ray image. In the second image, the at least one object is again classified and the at least one point is determined. Based on the classification of the at least one object in the first and second X-ray images as well as based on the determination of the at least one point in both X-ray images, the two images can be registered and a 3D position of the point relative to the at least one object can be determined.

In a case in which the at least one object includes two objects and the at least one point is a point of one of the two objects, the system may determine a spatial relation, i.e. a 3D orientation and 3D positioning, between the two objects based on the registered images.

Further, the system may determine a deviation of the 3D position and 3D orientation of one of the objects from an intended spatial relation of said object relative to another object. For example, the one object may be a drill, wherein it is intended to arrange that drill parallel to and on a trajectory through the other object which may be a bone or an implant.

The mentioned way of registering two X-ray images may, for instance, also be helpful for a 3D reconstruction and/or localization of an anatomical object, in which a known implant has been inserted. Localizing the implant enables a registration of images, and this in turn allows a determination of the 3D position (relative to the implant) of the drill's tip, which lies on the bone surface. The thus determined point may serve as an anchor point for the 3D reconstruction and/or localization of the anatomical object. Following this approach, it may be possible to determine multiple surface points, which means sampling the 3D bone surface at discrete points relative to the implant, leading to a point cloud. Each sample point added to this point cloud may reduce the ambiguities in the 3D reconstruction and determination of 3D position and 3D orientation of anatomy relative to the implant. If the drill's tilt is within the range of 10 to 55 degrees, this may also allow determining the 3D position and 3D orientation of anatomy (or implant) relative to the drill. Hence, even if a deterministic 3D model of the anatomy (e.g., a CT scan) is available, this procedure may be used to determining 3D position and 3D orientation. The method of sampling points may also be employed even without a known implant in fixed position to the bone. In such a case, reconstruction and/or localization and/or registration would proceed directly based on anatomy.

In the following, the influence of C-arm width, size of image detector, zoom, etc. on a 3D registration will be illustrated with examples. It is shown that in all of these examples determination of imaging depth is not required.

Influence of C-arm width: FIG. 1 depicts the left femur (denoted LF) and the nail implant with attached aiming device (denoted NAD). Furthermore, it shows the AP X-ray image (denoted 1.AP) and ML X-ray image (denoted 1.ML) and their corresponding focal points (denoted 1.FP.AP and 1.FP.ML). The 3D ball approximates the femoral head (denoted FH), and the dashed white circles are its 2D approximated projections in the images (denoted 1.FH.AP and 1.FH.ML). The C-arm has a width (here defined as the distance between focal point and image plane) of 1000 mm. The cones indicate the part of the X-ray beam passing through the femoral head. It is noted that throughout this application, we follow the convention to call images taken in a posterior-anterior direction "AP" images, and images taken in an anterior-posterior direction "PA" images. Similarly, we call images taken in lateral-medial direction "ML" images, and images taken in medial-lateral direction "LM" images.

Figure 2:
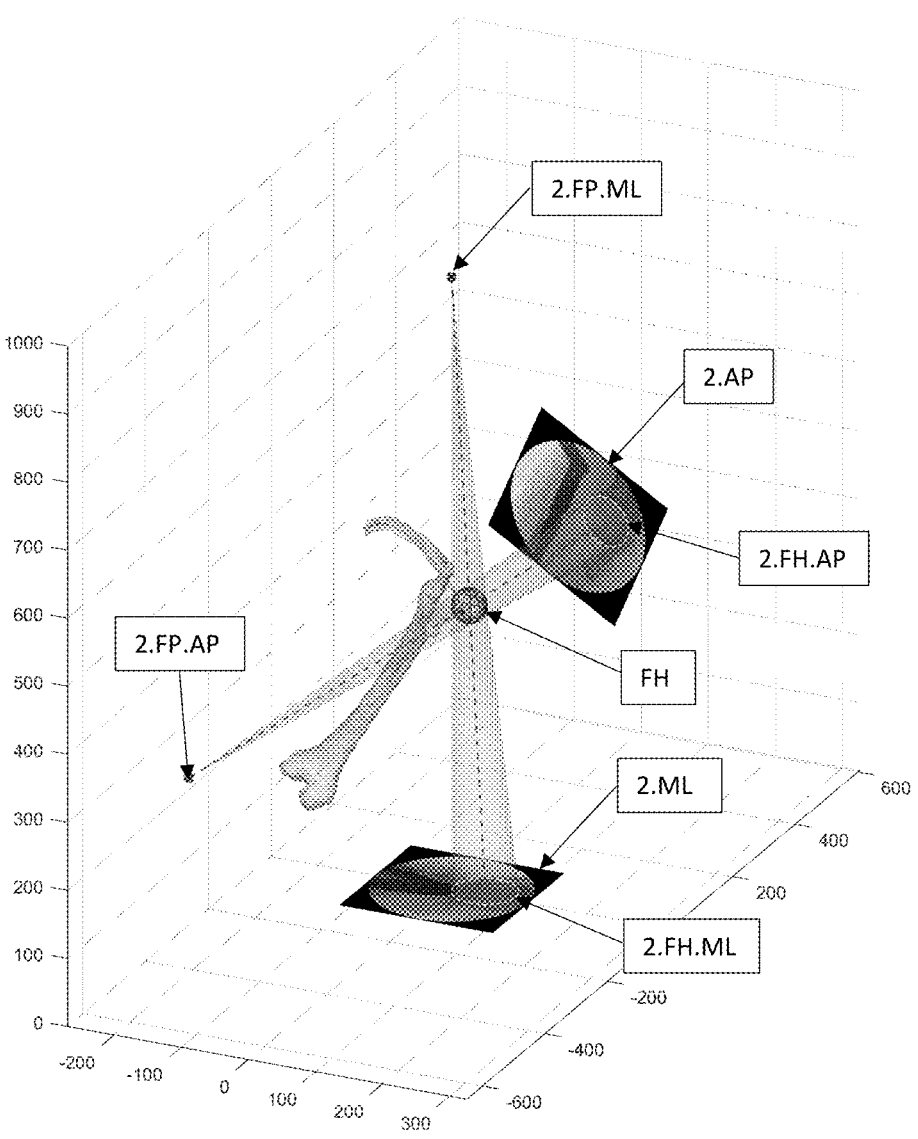
FIG. 2 shows an example for a 3D registration of AP and ML images and illustrates the effect of an incorrectly estimated C-arm width.

In FIG. 2, instead of the true 1000 mm, the C-arm width was incorrectly estimated as 900 mm. Hence, all objects in the image, including the femoral head (FH), appear smaller in the X-ray images than they should. Therefore, it seems as if the objects were shifted towards the AP image plane (denoted 2.AP) as well as towards the ML image plane (denoted 2.ML). The corresponding focal points are denoted 2.FP.AP and 2.FP.ML. A 3D reconstruction of the femoral head (FH) based on the 2D projections of the approximated femoral head (white circles 2.FH.AP and 2.FH.ML) remains unchanged compared to FIG. 1. The only parameter that is changed is the apparent imaging depth. The imaging depth, however, is not relevant in this scenario because the relative 3D position of femoral head and nail has not changed.

Figure 3:
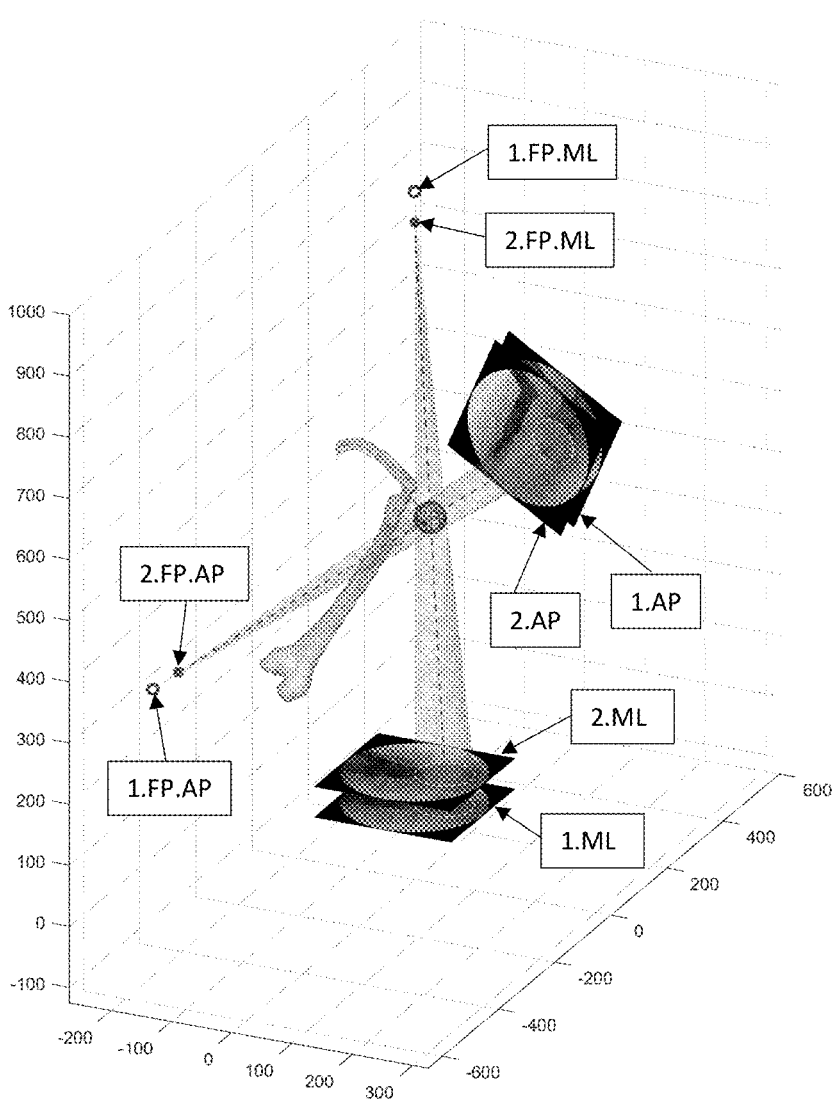
FIG. 3 compares the situations of FIGS. 1 and 2.

In order to illustrate that the only difference between FIG. 1 and FIG. 2 is the apparent imaging depth, FIG. 3 shows both scenarios simultaneously.

Figure 4:
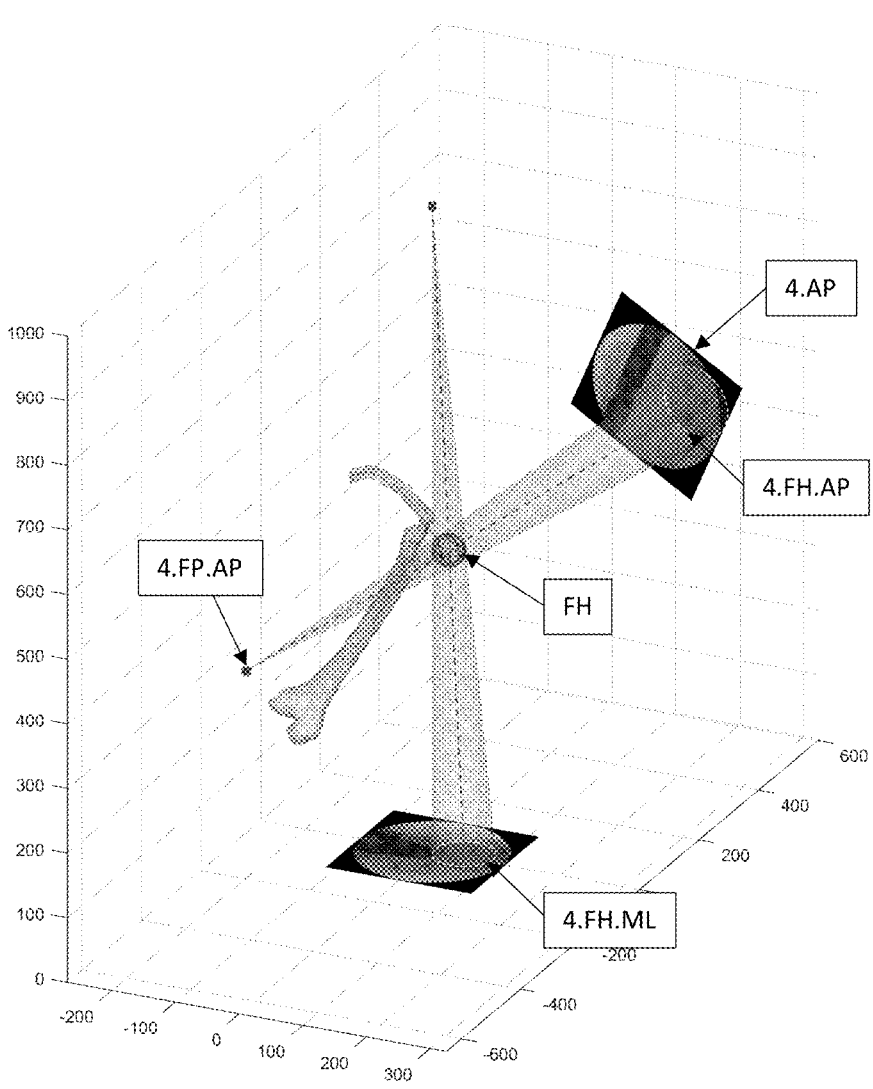
FIG. 4 shows an example for a 3D registration of AP and ML images and illustrates the effect of a zoom.
Figure 5:
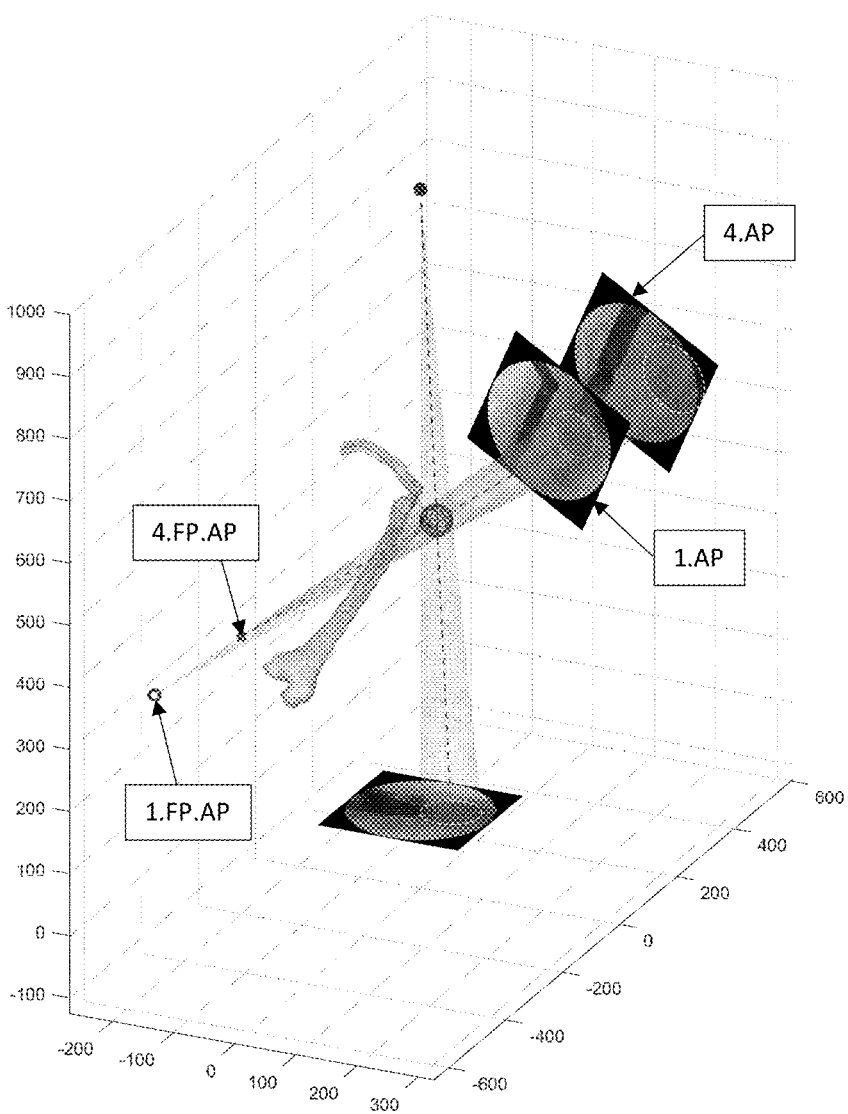
FIG. 5 compares the situations of FIGS. 1 and 4.

Influence of zoom: If one of the images was captured with a zoom factor, the objects appear bigger than without zoom. For FIG. 4, the AP image (denoted 4.AP) was captured with a zoom factor of 1.5. Hence, all objects in the image, including the femoral head (FH), seem as if they had been moved towards the focal point in AP (denoted 4.FP.AP). As before, a 3D reconstruction of the femoral head (FH) based on the 2D projections of the approximated femoral head (dashed white circles 4.FH.AP and 4.FH.ML) remains unchanged compared to FIG. 1. The only parameter that is changed is the apparent imaging depth. The imaging depth, however, is not relevant in this scenario because the relative 3D position of femoral head and nail has not changed. Analogous comments apply when both images have a zoom. FIG. 5 compares the situation with zoom (as in FIG. 4) and without zoom (as in FIG. 1).

Figure 6:
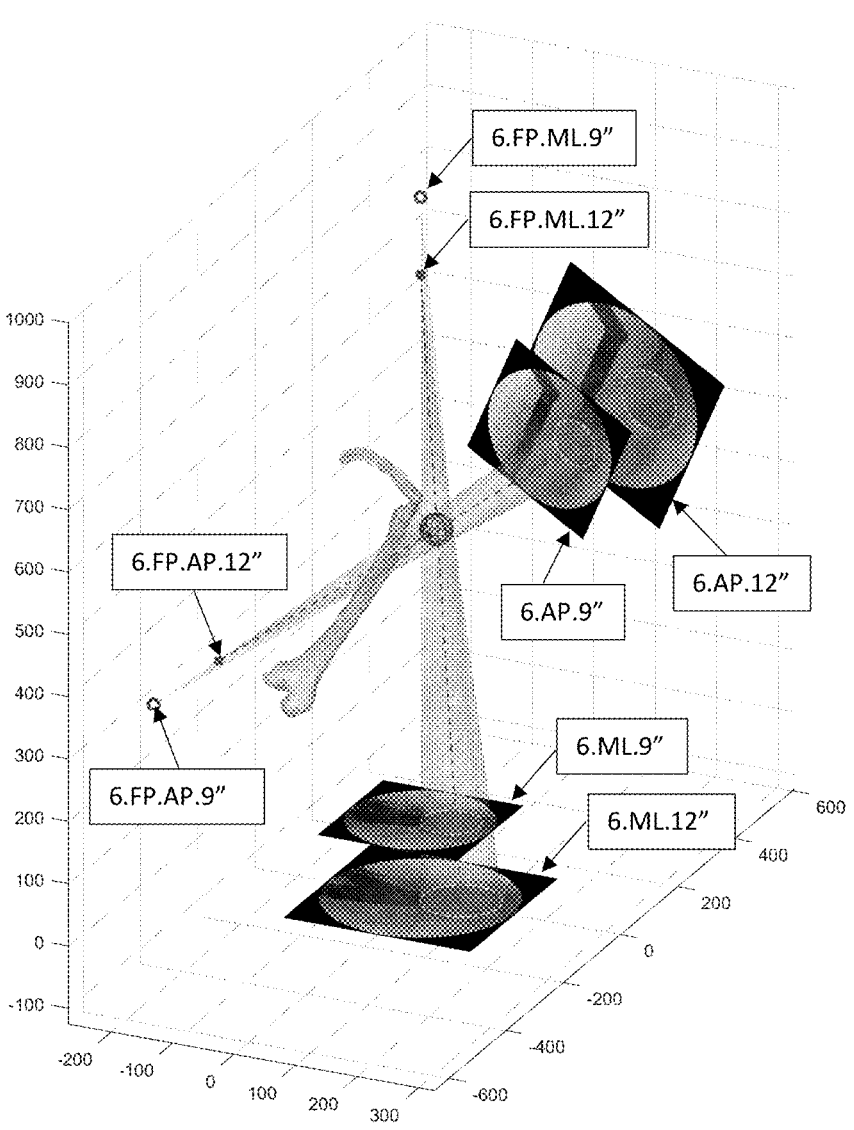
FIG. 6 shows an example for a 3D registration of AP and ML images and illustrates the effect of the X-ray receiver size.

Influence of size of X-ray detector: If the assumed size of the X-ray detector is 12" instead of the true 9", the objects appear bigger in the image, and it seems as if the objects had been moved towards the focal points in both images. This is shown in FIG. 6, where:

6.AP.9" refers to the AP image with 9" X-ray detector with focal point denoted 6.FP.AP.9"

6.AP.12" refers to the AP image with 12" X-ray detector with focal point denoted 6.FP.AP.12"

6.ML.9" refers to the ML image with 9" X-ray detector with focal point denoted 6.FP.ML.9"

6.ML.12" refers to the ML image with 12" X-ray detector with focal point denoted 6.FP.ML.12"

The effect is equivalent to a zoom factor that is applied to both images. Hence, the same conclusions as in the case of zoom may be drawn.

Measuring a Feature of a Classified Object

The current invention does not require an a priori calibration. Measurements may be performed in mm if there is a known object in the image located in the vicinity of (at a similar depth as) the structure to be measured. Since the known object has known dimensions, it can be used for calibrating measurements. This is similar to the procedure proposed by Baumgaertner et al. to determine a TAD value (cf. Baumgaertner M R, Curtin S L, Lindskog D M, Keggi J M: The value of the tip-apex distance in predicting failure of fixation of peritrochanteric fractures of the hip. J Bone Joint Surg Am. 1995, 77: 1058-1064.).

Example 1: A nail has been inserted, and an AP image is available. The nail has been identified and localized. Since the nail is located in the middle of the shaft and thus at a similar imaging depth as the depicted lateral cortex of the shaft, the known nail geometry can be used for calibration. This allows to provide a scaling for determining the distance between the nail axis and the lateral cortex of the shaft.

Example 2: It may even be possible to calculate a size of a different object (called "Object B") at a different imaging depth based on the intercept theorem if the imaging depth of Object A is known (e.g., because Object A is sufficiently big or because the size of the X-ray detector and the distance between image plane and focal point is known) and if there is information about the differences in imaging depths between Objects A and B (e.g., based on anatomical knowledge).

Handling Image Distortion for the Example of an Intramedullary Nail

In general, there are two ways of handling distortion of images, which may also be combined:

1. Deemphasizing regions in the X-ray image where distortion is known to be strong (e.g., border of images), placing more emphasis on regions less affected by distortion 2. Determining distortion and accounting for it These will now be illustrated at the example of an AP image of a femur with inserted nail.

Figure 7:
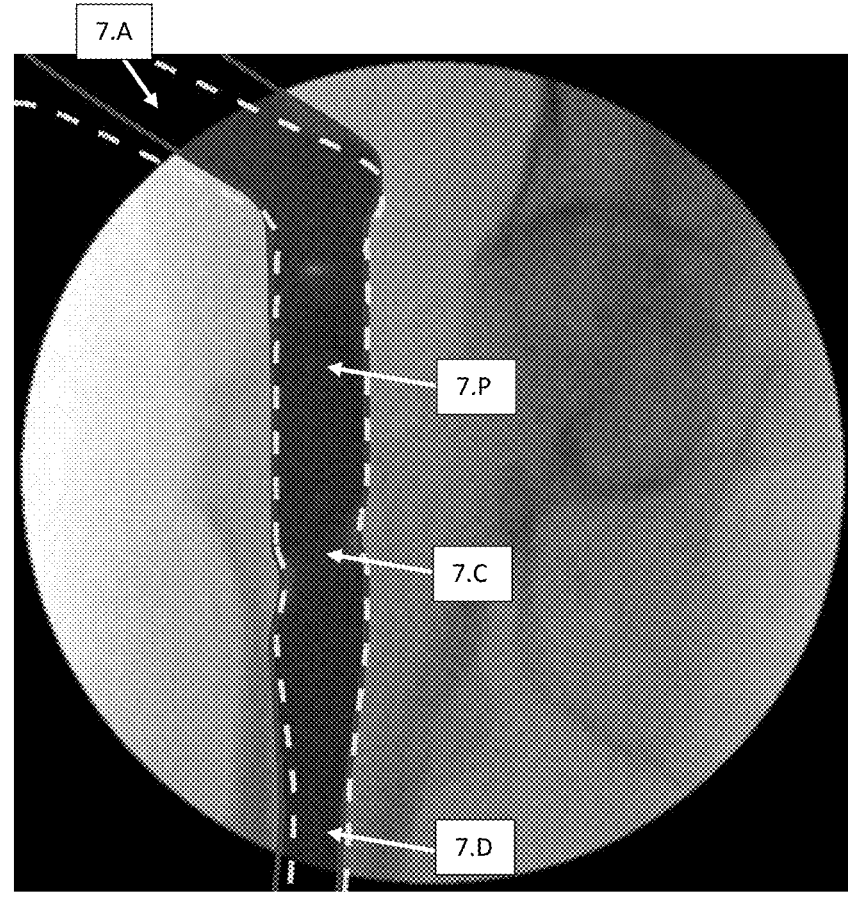
FIG. 7 shows an example for the image distortion for an intramedullary nail.

Re 1. The following letters are used in the labeling of FIG. 7. The solid line is the contour of a nail and aiming device as seen in a distorted X-ray image. The white dashed line shows the hypothetical outline of the nail and aiming device as they would be shown in an image without distortion.

7.D: Distal part of intramedullary nail

7.C: Central part of nail, including hole for neck screw

7.P: Proximal part of intramedullary nail

7.A: Aiming device

Typically, 7.D is located in a more distorted region of the X-ray image. Moreover, the precise location of 7.D is not as important when forecasting a trajectory for a screw inserted through the hole at 7.C. Thus, in a forecast of a screw trajectory, the locations of 7.C and 7.P may receive a higher weighting than 7.D, where the exact weighting may be determined based on their visibility and reliability of detection. A higher weighting on 7.C and 7.P may also be justified because these regions are closer to the region of interest (the screw hole and femoral head). Moreover, the appearance of 7.C carries information about the rotation of the nail around its axis.

Re 2. Distortion in an image may be determined by:

a) surgeries performed earlier (could be learned for a specific C-arm)

b) calibration before surgery: a known object (e.g., nail, k-wire, etc.) could be placed directly on the image intensifier/X-ray detector at a known distance to the image plane. This may also be used for determining the size of the X-ray detector and the distance between focal point and image plane.

c) images acquired earlier (could be learned by an algorithm during a surgery)

d) a database with typical distortion effects (e.g., typical pillow effect, earth's magnetic field, for typical C-arm positions). The device may use the knowledge that digital X-ray machines do not distort.

If such information is available, it may be utilized when matching a virtual projection of a model to a projection in the X-ray image. The distortion may be applied to the entire image, or specifically to the shape that is being matched.

Alternatively and/or additionally, distortion may be determined explicitly or implicitly during the process of matching the virtual projection of an object with known and deterministic 3D model (e.g., a nail) to the appearance of the object in the X-ray projection image. According to an embodiment, this matching may proceed along the lines described in the paper: Lavallée S., Szeliski R., Brunie L. (1993) Matching 3-D smooth surfaces with their 2-D projections using 3-D distance maps. In: Laugier C. (eds) Geometric Reasoning for Perception and Action. GRPA 1991. Lecture Notes in Computer Science, vol. 708. Springer, Berlin, Heidelberg. According to an embodiment, distortion may be described by a suitable mathematical model (e.g., a radial function and/or a sigmoidal function, as described by Gronenschild E., Correction for geometric image distortion in the X-ray imaging chain: local technique versus global technique, Med Phys., 1999 December; 26(12):2602-16). The distortion thus modeled may then be accounted for by introducing additional degrees of freedom into the parameter vector of the above cited paper by Lavallée et al. (1993) when matching the virtual projection to the projection in the X-ray image.

Handling an Exchange of the Positions of X-Ray Source and Receiver

Because X-ray imaging devices allow mirroring of images and this invention does not use a calibration reference body attached to the image detector throughout the surgery, an exchange of the positions of X-ray source and receiver may not be detected, even if the treatment side (left or right bone) is known. A user could be required to provide information about whether or not the mirroring function is activated.

However, even in the absence of such information, an exchange of the positions of X-ray source and receiver may be detected. This is because a tool or instrument in the X-ray image viewed from an imaging direction much smaller than 90 degrees covers a large range in imaging depth. Hence, an exchange between X-ray source and receiver may be detected because the part of the tool or instrument closer to the imaging plane (receiver) will be depicted smaller than the one further away.

Method for Determining X-Ray Image Rotation/Mirroring/Flipping

A method is provided to enable the system to determine X-ray rotation, mirroring, and flipping. This may be used, for instance, to display the X-ray image such that the nail appears exactly like it is positioned in reality in front of the surgeon.

The following are known to the system, based on the surgical procedure to be performed:

The patient's positioning (e.g., lying on his/her back)

The C-arm's position (e.g., image intensifier is medial, X-ray source is lateral)

Which part of the patient's body is being operated on (e.g., left/right leg: This may be known, e.g., based on a previous proximal procedure, user input, or scanning the nail packaging)

A detection of mirroring (i.e., determining which side is anterior and which side is posterior) may be based on determining the direction of an implant, possibly supported by determining an imaging direction onto anatomy (e.g., the condyles are pointing downwards in the image if the patient lies on his/her back). Alternatively, an instruction may be provided to the user to point a tool (e.g., a drill) in a specific direction, which may then be used to identify this direction as anterior or posterior.

Figure 16:
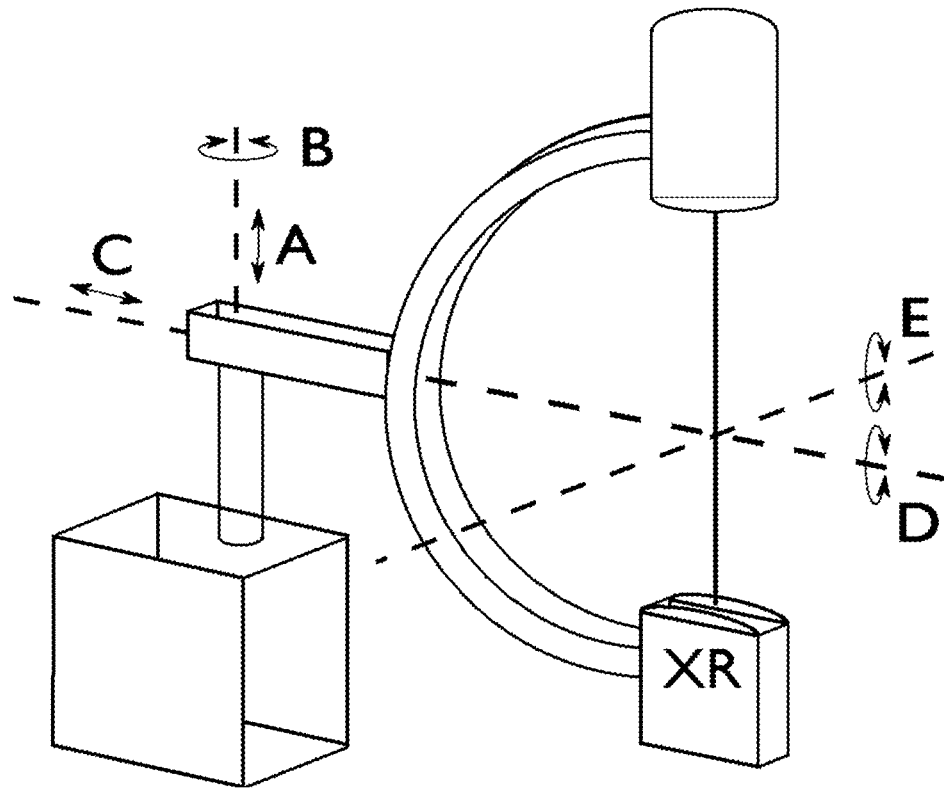
FIG. 16 defines a C-arm's rotation axes.

Method for Positioning a Target Object/Structure in the C-Arm's Field of View from a Desired Viewing Direction For the definition of a C-arm's rotation axes, it is referred to FIG. 16. In this figure, the X-ray source is denoted by XR, the rotation axis denoted by the letter B will be called the vertical axis, the rotation axis denoted by the letter D will be called the propeller axis, and the rotation axis denoted by the letter E will be called the C-axis. It is noted that for some C-arm models, the axis E may be closer to axis B. The intersection between axis D and the central X-ray beam (labeled with XB) is called the center of the C-arm's "C". The C-arm may be moved up and down along the direction indicated by the letter A. The C-arm may also be moved along the direction indicated by the letter C. This terminology will be used throughout this application. The distance of the vertical axis from the center of the C-arm's "C" may differ between C-arms.

In the following, methods are proposed to provide instructions to the user how to adjust the C-arm such that a target structure appears at the desired location in the X-ray projection image, and the structure is viewed from a desired imaging direction (e.g., a locking hole should appear round, and the nail axis projection should run through the center of the X-ray image). Even if the necessary rotation and translation, e.g., based on localizing an object, were correctly determined, it may not be trivial to determine suitable user instructions for a repositioning of the C-arm. As shown in FIG. 16, a C-arm has multiple rotation and translation axes. Moreover, it is also possible to move the C-arm on its wheels to a different position in the operating room. This also allows translations parallel to the floor and rotations around an axis parallel to the vertical axis, yet which typically has a large distance (greater than 1 m) from the vertical axis.

The many available options of moving the C-arm make it difficult for the user to decide which option is the best to reach a desired position (for a desired imaging direction) most quickly or with the least effort. Moreover, there are also constraints resulting from the OR setup that prevent the user from moving the C-arm to certain positions. Hence, the user may in some instances choose to move the patient (or the table) rather than the C-arm, especially in procedures dealing with an upper extremity.

A method may be proposed to (i) determine the necessary information on how to reposition the C-arm/and or patient, to (ii) translate this information into guidance to the user, choosing from the available means of moving the C-arm (either by translation along or by rotation around the C-arm's axes, or by moving the C-arm on its wheels) or moving the patient, and to (iii) determine the necessary amount of movement in each case.

In other words, a method of assisting in adjustment of an imaging direction of a C-arm based imaging device may comprise the steps of receiving information of a current imaging direction, receiving information of a target imaging direction, determining a first one out of the plurality of means for rotational and translational movements of the X-ray source and detector and an amount of movement for that first means, achieving an imaging direction closest to the target imaging direction. It will be understood that such a method may be implemented as software program product causing a system to perform the method.

These methods may consider possible constraints imposed by the C-arm's construction and by the OR setup, and they may choose those movements that are easiest for the user to perform and require the smallest number of movements.

These methods may determine a current imaging direction on the basis of an X-ray image. For example, the viewing or imaging direction may be determined based on anatomy (e.g., using the patent application filed by Blau on 23 Aug. 2018) and/or localizing the target structure (or object), possibly taking into account a priori geometric information about implants, instruments, or anatomy, and further possibly considering the target structure's 3D position and 3D orientation in the coordinate system spanned by the image plane, further possibly taking into account the typical OR setup for the current surgical procedure (position of the patient on the OR table, position of the C-arm relative to the table, position of any objects that could prevent the C-arm from being moved to a certain position relative to the table/the patient), and further possibly considering the typical rotation axes of the C-arm.

The typical position of the patient relative to a C-arm may be assumed known, e.g., for a femoral nailing procedure:

patient lying on his/her back, known treatment side, image receiver between the patient's legs. Additionally or alternatively, the user may choose the OR setup from a provided set of options. Those may be based on information the system gathers from, e.g., scanning the package of the implant, a previously performed part of the surgical procedure where the system learned, e.g., the positioning of the patient on the OR table, which implant is used, and/or where the C-arm machine is positioned relative to the table (e.g. between the legs of the patient).

It may not be trivial to translate a computed deviation from a desired position/orientation into instructions for adjusting the C-arm, as these instructions are supposed to be as easy to execute as possible. Instructions not requiring moving the C-arm on its wheels may be preferable because moving the C-arm on its wheels may be less accurate and more difficult to perform in an OR setting. Generally, it may be preferred to keep the number of instructions small. A neural net may assist in this entire procedure.

For instance, in case a large rotation around the vertical axis is required, this should be performed by moving the entire C-arm on its wheels because this may allow an isocentric rotation around the target structure (keeping the target structure close to the central C-arm beam). If the required rotation is with respect to an axis parallel to the C-arm's vertical axis and the rotation is relatively small, the vertical axis of the C-arm should be used. It must be kept in mind that such rotation includes a relatively large translational component if the desired rotation axis is far from the C-arm's vertical rotation axis, but any such translation may be accounted for when determining any potentially required translation. As explained above, a rough determination of the imaging depth may be possible (up to a few centimeters). This may be sufficient for computing, for instance, the translation in AP direction resulting from a rotation around the C-axis because the distance of the C-axis from the target structure is roughly known. In addition, the offset between the C-axis and the central X-ray beam may be computed from a rotation around the C-axis. Moreover, any translation of the C-arm automatically includes a rotational component due to the fact that a perspective projection applies.

Making rough assumptions on the 3D positions and 3D orientations of the C-arm's axes relative to the target object/structure may be sufficient for the first iteration step of the positioning procedure, which occasionally may result in a position close enough to the desired position. For higher accuracy or to reach a sufficiently accurate position with the least number of steps, the system may in subsequent steps use the information gathered from previous iteration steps, which may allow to more accurately determine the 3D position and 3D orientation of axes relative to the target object/structure. As an example, if a translation along or rotation around more than one C-arm axis is necessary to reach the desired position of the C-arm, the system may instruct the user to move or rotate the C-arm around one axis, for instance, a rotation around the C-axis. This may allow to get closer to the desired position and at the same time to determine the 3D position and 3D orientation of the C-axis relative to the target object and to determine the offset between C-axis and the center of the C-arm's "C".

Alternatively, depending on available a priori information, the 3D position and 3D orientation of the C-arm's axes relative to the target object/structure may be determined by either (i) moving the C-arm along two axes perpendicular to each other (in case the axes do not intersect, a parallel of one of the axes must make a right angle with the other axis), or (ii) rotating the C-arm along two axes perpendicular to each other (in case the axes do not intersect, a parallel of one of the axes must make a right angle with the other axis), or (iii) moving the C-arm along one axis and then rotating the C-arm around another axis parallel to the movement axis, for instance: a translational movement in anterior direction combined with a rotation around the vertical axis, or a rotation around the C-axis combined with a rotation around the propeller axis, or a translation in proximal direction combined with a translation in posterior direction.

As an example, for a lateral distal locking procedure of an antegrade femoral nail (with the C-arm positioned between the patient's legs, the patient positioned on his/her back), an anterior translational movement of the "C" would, on the one hand, result in a rotation of the viewing direction around the nail axis, which may enable a more precise calculation of the 3D position of the target object with respect to the C-axis in order to more precisely determine the imaging depth. On the other hand, the system may determine the rotation of the nail around its axis relative to the OR floor. When, at a later point in time, calculating guidance instructions on anterior/posterior translational movements the system may compute the required translation by using simple trigonometric relations, taking into account the impact of the above determined rotation of the nail around its axis relative to the OR floor on the required translation along the vertical axis. This information may also be utilized when calculating other movement instructions provided by the system: E.g., when calculating a required rotation around the vertical axis, the distance between the object and the vertical axis may be more precisely determined (as the distance of the vertical axis to the C-axis may be more precisely determined). Hence, because the distance between the central X-ray beam and the C-axis has already been determined, the effect of translation in proximal distal direction caused by the rotation around the vertical axis may be taken into account more precisely.

In practice, it may be sufficient to determine, in a first iteration step, one or two means of movement or rotation to approximate the final desired position. By observing these one or two movements/rotations the system may obtain sufficient information about the 3D position and 3D orientation of the axes relative to the target object/structure so that, in a second iteration step, all remaining necessary steps to reach the final desired position may be determined with sufficient accuracy and provided to the user. As described below in the section "Example for a potential processing workflow for a distal locking procedure" the system does not need a very precise positioning of the C-arm, e.g., a perfectly circular projection of the round hole may not be required.

In case the user moved the patient rather than the C-arm in response to a system instruction, a check of the image background may help detect such movement and prevent an incorrect determination of movement/rotation axes "Image background" in the previous sentence may be every not fully X-ray translucent objects that do not move together with the patient (e.g., parts of the OR table). Employing a simple image difference analysis may reveal whether or not the C-arm was moved. It may be required in this context that there be no digital image rotation at the C-arm in between C-arm movements and image acquisitions.

Based on the initial positioning of the target structure within the image and viewing direction on the target structure, the system may decide on which movement to start and/or to proceed with.

Instructions may be provided how to rotate the C-arm around the C-axis and how to move the C-arm up or down. If the target structure is not positioned in the center of the C-arms "C", a translation instruction may be provided how to restore the previous position in the X-ray image, or how to reach a desired position. Instructions may be provided how to rotate the C-arm around its vertical axis. This may take into account the typical C-arm geometry (distance between vertical axis and center of the C-arms "C"), and the specific C-arm geometry may be learned by the system from a previous rotation. If the target structure would not appear in the desired location in the X-ray image or would no longer appear in the desired location after rotation, an instruction on how to translate the C-arm may be provided. No translation instruction is provided if the target structure's position in the X-ray image is already correct and will remain correct after rotation (e.g., if the C-arm is moved on its wheels such that the target structure remains in the center of the C-arms "C").

This procedure may also be applied analogously to other axes of the C-arm, e.g., the propeller axis.

Regarding an optimized adjustment of a C-arm, the following general aspects may be mentioned as a summary.

First of all, it is intended to use only one means for translation or rotation of the C-arm device so as to adjusts the position and orientation of the imaging direction as close as possible or at least with a sufficient accuracy to the target imaging direction, i.e. an optimal direction.

If necessary, a second means may be suggested to be used so as to further adjust the imaging direction. Further means may be utilized to further improve the accuracy.

The current imaging direction, i.e. the starting point for the adjustment, may be determined based on a localization of an object or structure in an X-ray imaging generated with the current imaging direction. It will be understood that the object or structure may also be a sub-structure and may be an anatomy, an implant or an instrument/tool, or may be a combination of such objects.

The target imaging direction may be identified based on a geometrical aspect, a 3D position and 3D orientation of which is known. It is noted that such geometrical aspect may also be known from a pre-operative planning, with the geometrical aspect being available from a data base.

Further, the position and orientation of an object may be generally known relative to the C-arc of the C-arm based imaging device. In a typical operation room setting, an anatomy may be arranged relative to a C-arm device in a known way allowing a prediction of the imaging direction. The system may in some cases provide information for validation to a user.

Alternatively or additionally, the system may learn how a user tends to utilize the translation and rotation of a C-arc and may take into account that way of using. For example, the system may calculate a rotation axis or a translation of the C-arm device relative to an object from two images where the imaging direction is rotated about that rotation axis or translated between generation of the images. In particular, the system may learn whether a user tends to move the C-arm device with an amount being more or less then instructed and may take that into account when providing further instructions to move the C-arm device.

Example for a Potential Processing Workflow for a Distal Locking Procedure

The following distal locking procedure is described for a long antegrade nail. Nevertheless, it may also be applied to a retrograde nail, which will be locked proximally. The following locking procedure is presented for a hole whose axis lies approximately in ML direction, but it may also be applied to a hole whose axis lies in a different direction, e.g., AP.

For such a procedure, it may be assumed that a complete 3D model for the target object (i.e., nail) is available. Nevertheless, the procedure may work even if only an incomplete or partial 3D model is available, e.g., only approximate information about the nail's shape is known (for instance, a cylindric object whose diameter slightly decreases toward the tip, with cylindric locking holes).

A locking hole will be called "target structure" in the following. In principle, it is sufficient to know the relative 3D position and 3D orientation between tool (e.g., a drill, an awl, a sleeve, or even an implant such as a screw) and target structure. Hence, in the following, both target object (nail) and target structure (locking hole) will be discussed. In this description, it is assumed that a round hole will be locked first.

1. The user acquires an X-ray image of the nail in approximate ML direction.

Figure 20:
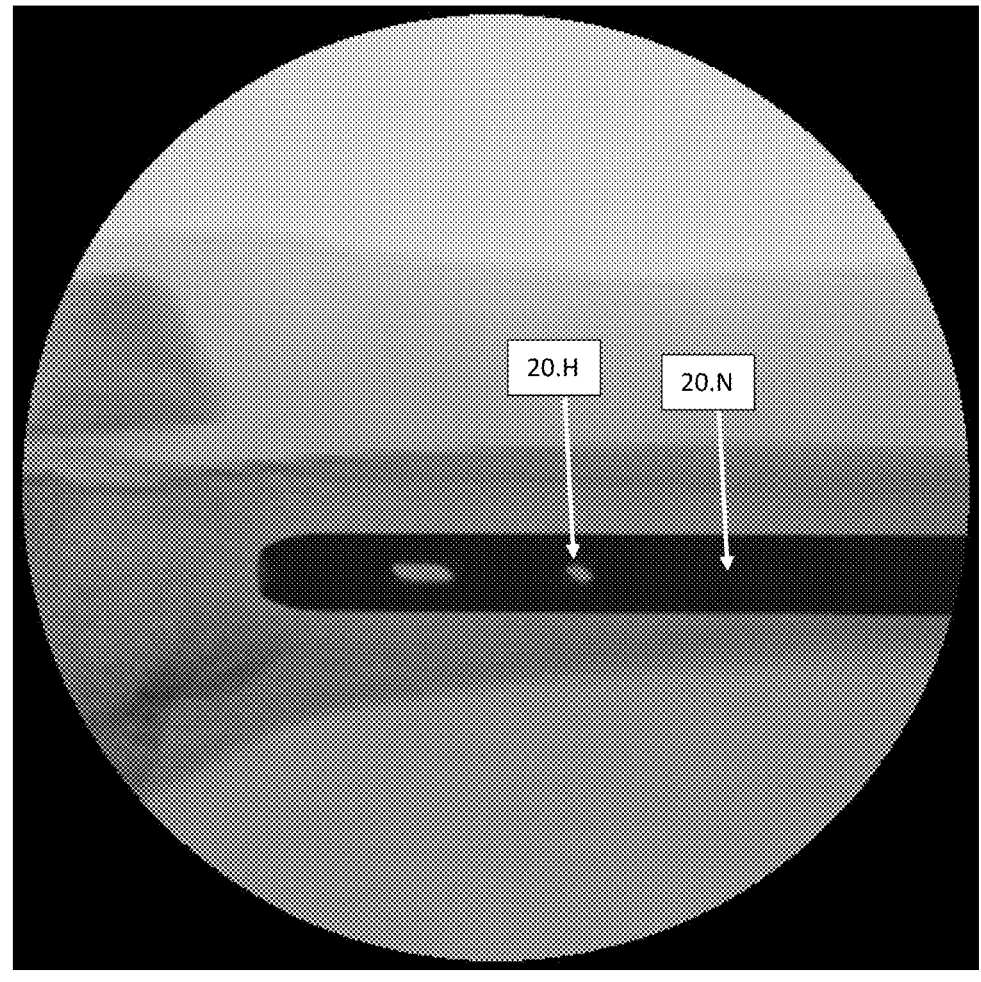
FIG. 20 is an X-ray showing the distal part of a nail from an incorrect imaging direction.
Figure 21:
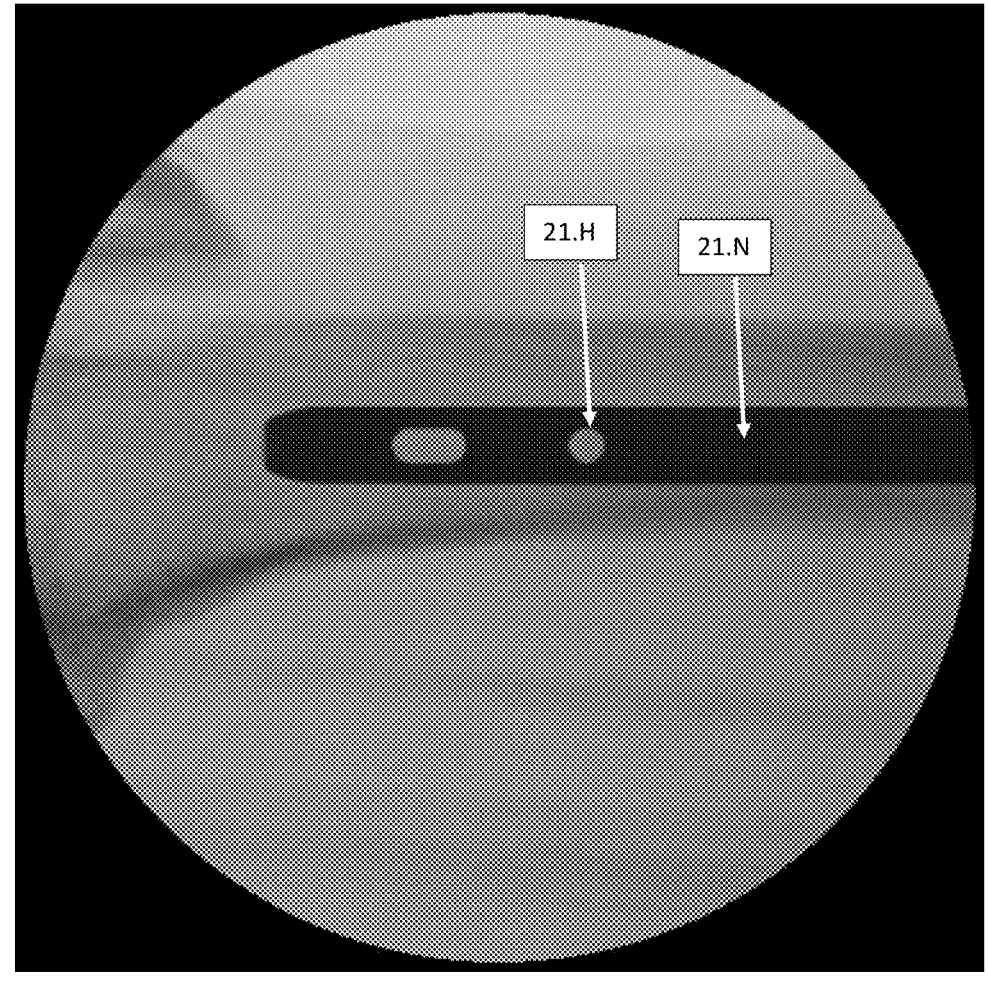
FIG. 21 is an X-ray showing the distal part of a nail from a correct imaging direction.

2. The system may determine the imaging direction onto the target structure (e.g., by detecting (in 2D) or localizing the target object). The system may retrieve or determine the target trajectory (or possibly, a target plane) relative to the target object or structure. The system may then determine and inform the user how to adjust the C-arm to reach the desired imaging direction onto the target trajectory. Often, the desired imaging direction is aligned with the target trajectory, in which case the distal locking hole will be depicted as a circle. FIG. 20 is an X-ray image where the nail, labeled 20.N, is visible with a non-circular locking hole, labeled 20.H. Thus, the imaging direction is not the intended ML imaging direction. FIG. 21 is an X-ray image where the nail, labeled 21.N, is viewed from a true ML imaging direction, as is evident by the circular locking hole, labeled 21.H.

It may be desirable that the nail axis run through the image center and the locking hole be close to the image center. This may be desirable if there are further holes to be locked without readjusting the C-arm. Hence, ideally the hole should lie on the central X-ray beam. The C-arm adjustment is performed iteratively and may be completed with a new X-ray image satisfying said requirements.

Figure 22:
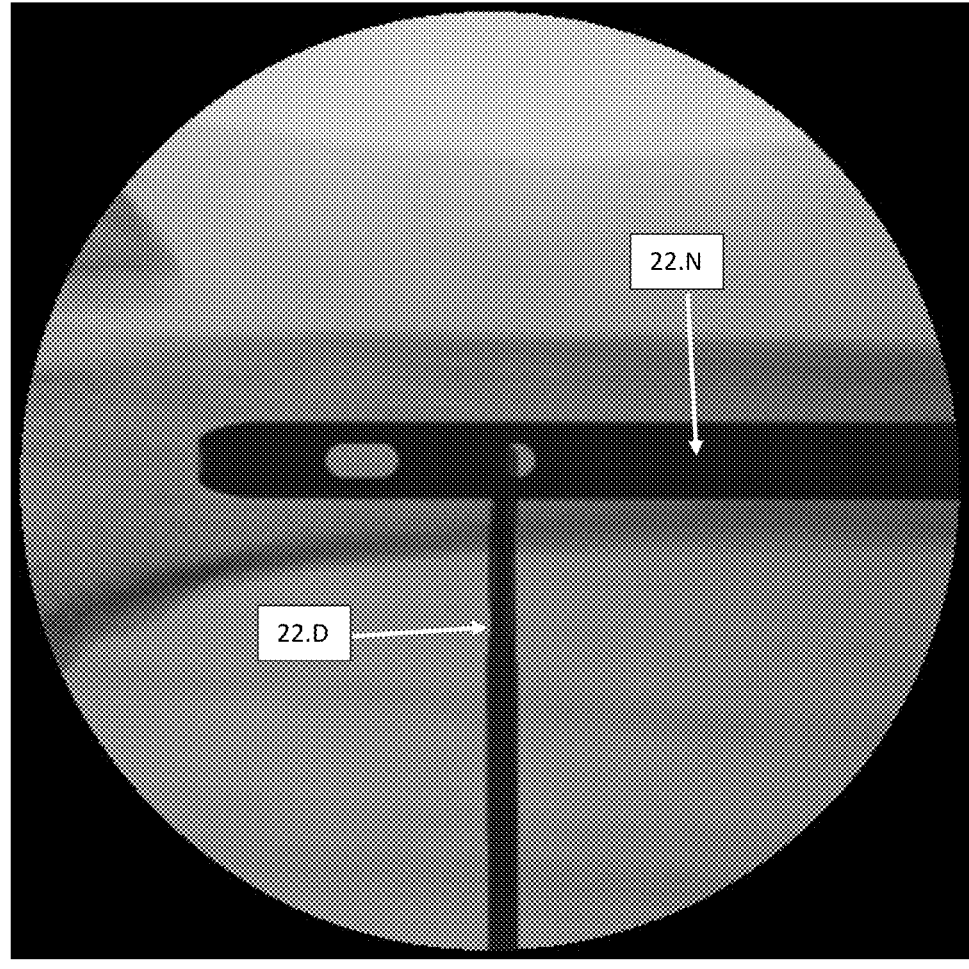
FIG. 22 is an X-ray showing a nail and a drill with an incorrectly placed drill tip.
Figure 23:
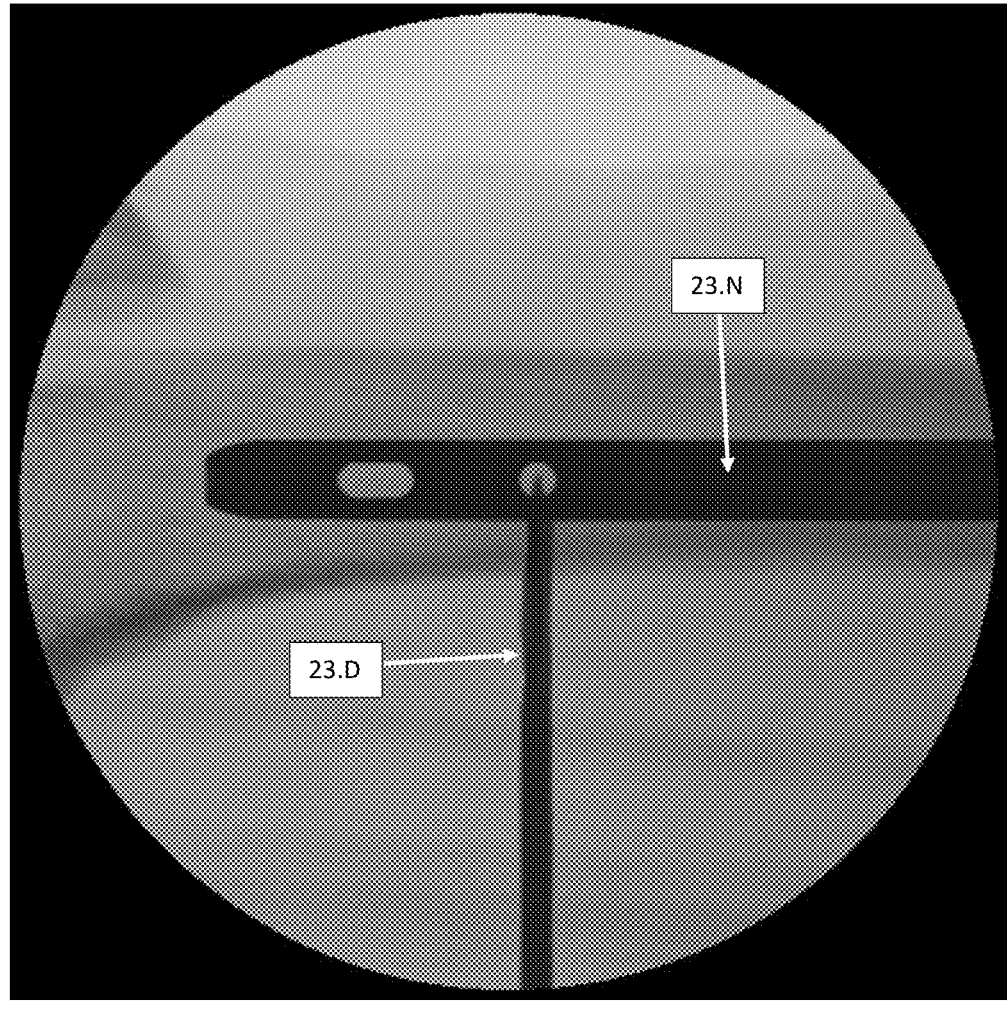
FIG. 23 is an X-ray showing a nail and a drill with correctly placed drill tip.

3. The system may now highlight the center of the locking hole in the X-ray image, which the tool should aim for. This highlighted (target) point lies on the target trajectory and, in the described scenario, is the center of the circle. The system may then detect in 2D the tool's tip and compute the required movement of the tip to reach the target point. The system may support the user in an iterative process (each iteration consisting of acquiring a new X-ray image and repositioning the tool) to reach the target point. FIG. 22 shows an X-ray of a nail (22.N) and a drill (22.D) with an incorrectly placed drill tip. FIG. 23 shows an X-ray of a nail (23.N) and a drill (23.D) with correctly placed drill tip.

4. Once the tool's tip (here, a scalpel) lies on the highlighted point in the X-ray image, the surgeon may make an incision, insert the drill (possibly with a soft-tissue protection sleeve), and Step 3 is repeated. The user may then decide (as in the conventional procedure) to align the drill with the target trajectory without moving the drill's tip.

5. The C-arm is rotated, e.g., around the C-axis by, e.g., 25 degrees, and a new X-ray image is acquired. The system may again localize the target object (or possibly only the target structure). Based on the a priori knowledge that the tool's tip lies on the target trajectory (which remains in a known 3D position and 3D orientation relative to the target object/structure), the relative 3D position and 3D orientation between drill and target object/structure may be determined. Even if the drill's tip in distal-proximal direction no longer lies exactly on the target trajectory, the system may calculate the corresponding deviation. This is because, in case the C-arm was rotated around the C-axis, it may be sufficient to have the a priori information that the drill's tip lies in a plane spanned by the target trajectory and nail axis.

Now the system may compute the deviation from the target trajectory and may thus inform the user, for instance, by displaying the required angle corrections in proximal-distal and anterior-posterior directions. If required, the system may also instruct the surgeon how to adjust the tool's tip position in proximal-distal direction. Furthermore, the system may also calculate the penetration depth, in this case, e.g., the distance between drill tip and nail, and thus inform the user. This Step 5 may be performed iteratively, by iterating between acquiring a new X-ray image, providing information/instructions to the user, and readjustment of the tool.

Informing the user may be done on a display and/or acoustically. An advantage of an acoustic information may be that the surgeon need not look away from the drill and may thus achieve the right direction for drilling with fewer iterations.

6. Step 5 may also be performed during drilling in order to adjust the drilling direction and/or obtain information on how much further to drill. (This is independent of the fact that, in a typical distal locking situation, drilling continues, after hitting the nail hole, up to the next cortex.)

Locking of a Further Hole (e.g., an Oblong Hole):

In order to save time and X-ray exposure, a procedure is presented in the following for locking a further hole (hereafter assumed to be an oblong hole) after a first hole has been locked as described above.

Assuming that the target trajectory for the oblong hole lies in the same plane as the first hole, the C-arm is rotated back to its original position (where it was before Step 5 was performed), showing the first hole (with or without screw) as a circle. Therefore, the nail axis again runs through the center of the X-ray image, and the oblong hole is in the proximity of the image center. No readjustment of the C-arm is necessary, unless a correction of the rotation around the C-axis is required because the original angle was not reached precisely enough. The oblong hole thus appears with maximal diameter in AP direction, but compressed in the perpendicular direction. If, on the other hand, the target trajectory for the oblong hole does not lie in the same plane as the first hole, the required readjustment for the C-arm may be supported by the system, as described above.

Because the system knows, from locking the first hole, the approximate distance between bone surface and nail in medial-lateral position, it may use this value (and possibly a statistical model of the bone) to correct the target position of the drill's tip (cf. Step 3 above). Hence, in order to hit the oblong hole in the center (with respect to both AP direction and distal-proximal direction), the target point in the 2D X-ray will not appear in the center, but shifted in distal-proximal direction.

Figure 17:
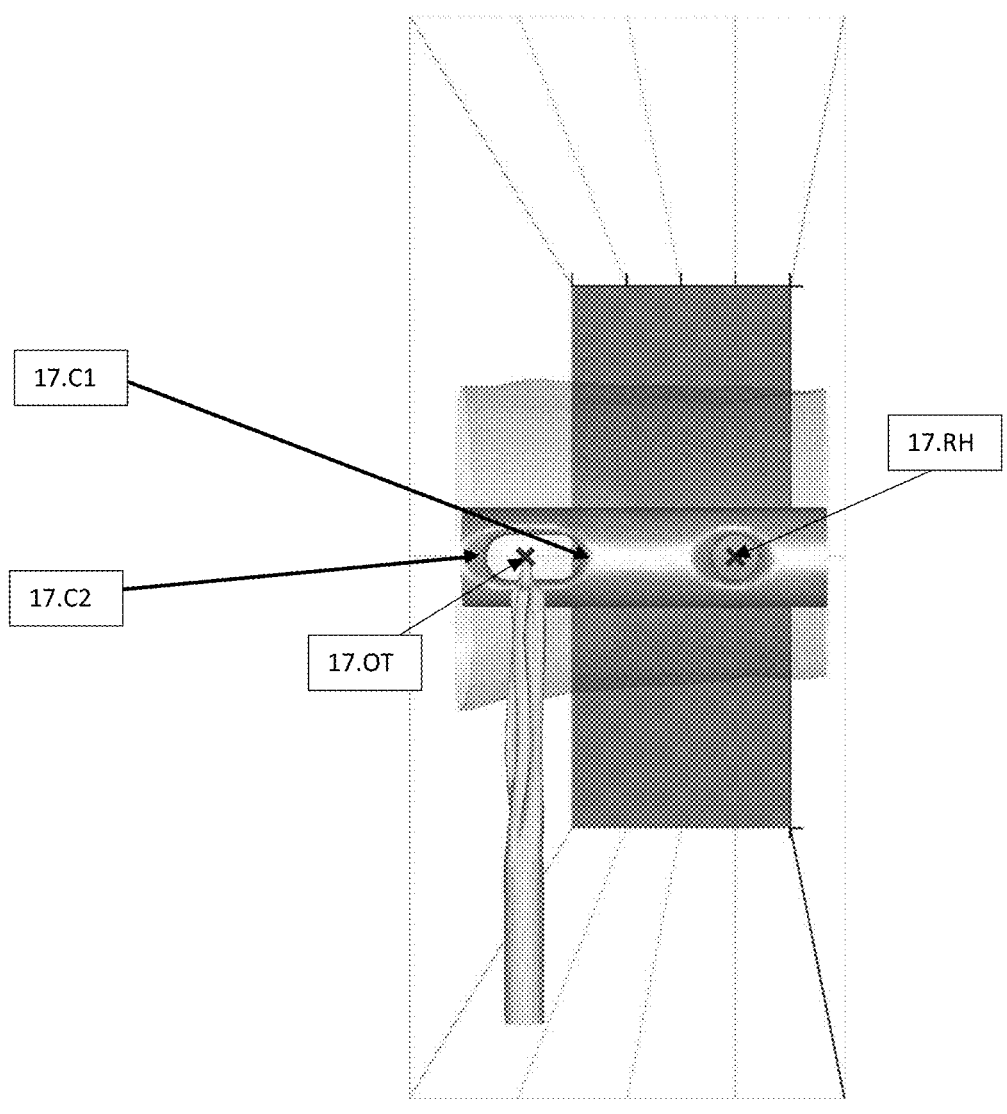
FIG. 17 shows round and oblong holes of a nail, including the chamfer.

In FIG. 17, the round nail hole denoted by 17.RH is perfectly circular in 2D, i.e., in an X-ray. Since the opening tool tip (denoted by 17.OT) has a certain distance from the center of the oblong nail hole due to its position on the bone surface, it is not in the 2D center of the oblong nail hole, though the tip is placed perfectly on the oblong nail hole center trajectory in 3D. The two black arrows denoted by 17.C1 and 17.C2 show the chamfer, which appears with different sizes on both sides of the oblong nail hole due to the perspective view.

Any potential inaccuracies in distal-proximal direction may not matter because an incorrect positioning of the tool's tip in distal-proximal direction may be detected and computed after (approximately) aligning the tool with the target trajectory, rotating the C-arm around the C-axis, and acquiring another X-ray image. If necessary, instructions for correcting the tool's tip position in distal-proximal direction may then be given. As discussed above in Step 5, it may be sufficient that the tool's tip lies in a plane spanned by target trajectory and nail axis. The remainder of the procedure follows the steps for the first hole.

If the oblong hole is tilted with respect to the nail axis, the tilt may be accounted for when rotating the C-axis, with a potential finetuning supported by the system.

The entire discussion applies to round holes as well. Moreover, it is also possible to lock further holes following the same procedure.

As discussed above, the viewing direction onto the hole need not be perfect (i.e., with maximal projected hole width and height, e.g., perfectly circular for a round hole) to position the drill's tip on the target trajectory. Depending on the available a priori information and how strict the requirements for an angle determination are (these are the less strict the smaller the distance to be drilled between bone surface and nail is), the viewing direction onto the hole may deviate more or less from the target trajectory. For example, if an AP image was acquired, the distance between lateral bone surface and nail along the target trajectory may be approximately determined. (Alternatively, the distance is simply estimated.) Based on this information and a lateral X-ray image, the point in a 2D X-ray image where the drill's tip should be positioned in order to lie on the target trajectory, may be computed (and then displayed) also based on an oblique viewing angle, analogously to the discussion above. This point need not perfectly lie on the drill's trajectory. Rather, the deviation from this point (in 2D spatial coordinates), as determined in the 2D X-ray image based on the estimated or previously determined distance between bone surface and nail along the locking trajectory, may be used to compute a new target trajectory. The new target trajectory may then be used in the next image for orienting the drill. This may make it easier for the surgeon to position the drill's tip on the right point because it need not be hit perfectly. Moreover, it may also allow a higher accuracy in the orienting the drill for hitting the target hole.

Assuming that a sufficiently precise position of a point of a second object relative to a geometrical aspect of a first object known, it may be possible to perform a 3D reconstruction and/or determination of relative 3D position and 3D orientation by image registration.

A deviation from the original target trajectory may also be solved by the following method. In a first image the instrument may be placed on an arbitrary point (which may or may not lie on the target object) and in a second image (obtained from a different viewing direction) the instrument's inclination may have changed (e.g., by aiming approximately to the target trajectory) but the instrument's tip remains on the same position. Based on a localization of the target object/ structure, both images may be registered, which may allow a determination of the 3D position of the point relative to the target object. This point may then be used to determine, with sufficient accuracy, the relative 3D position and 3D orientation between tool and target object/structure.

In case, in Steps 5 or 6 above, the tool's tip is occluded by the target object (e.g., a nail made from steel) and therefore localization is not sufficiently accurate, the system may provide instructions how to make the tool's tip visible to the system. This may proceed by the system calculating and giving instructions how the C-arm needs to be repositioned (e.g., a rotation around C-axis instead of rotation around axis perpendicular to nail axis). In case that the tool's material absorbs sufficiently more X-rays than the target object (e.g., tool made of steel, nail made of titanium), this may also be achieved, e.g., by increasing voltage and/or current, or choosing a different C-arm program setting.

Additionally or alternatively, the system may match a statistical 3D model of the bone and thus determine the 3D position of the nail relative to the 3D position of the bone, thus enabling a determination of the needed locking screw length in 3D.

Figure 18:
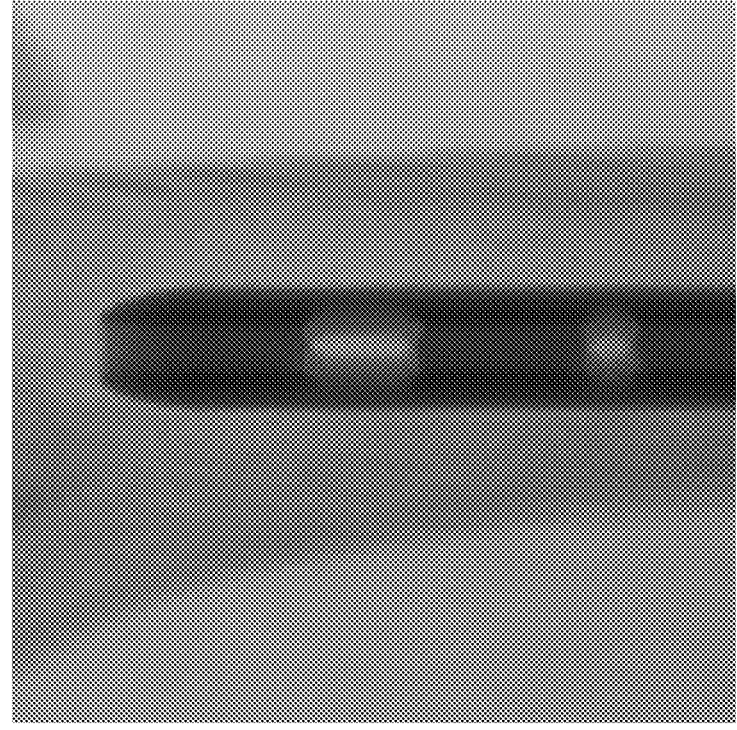
FIG. 18 is an X-ray showing a titanium nail rotated around its axis by 25 degrees away from the locking plane.
Figure 19:
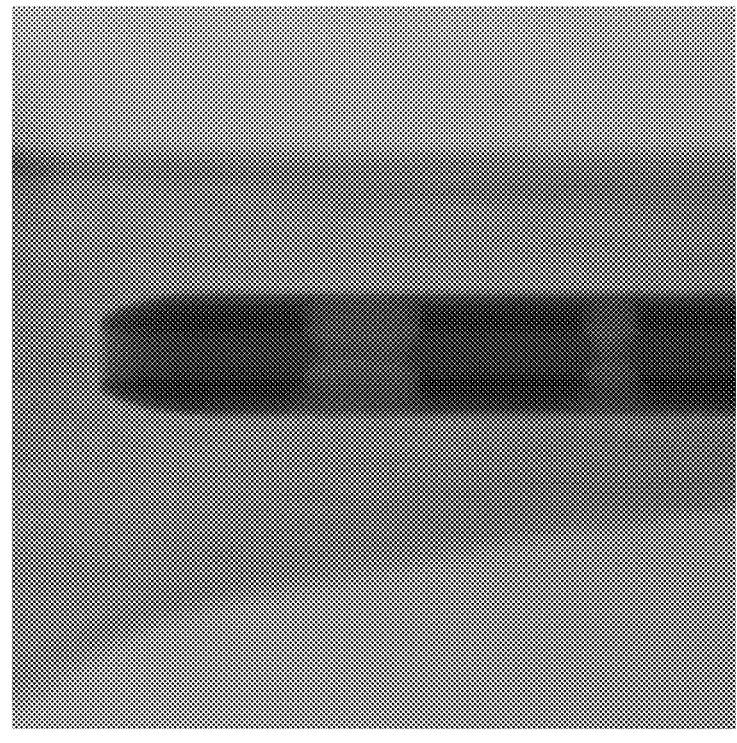
FIG. 19 is an X-ray showing a titanium nail rotated around its axis by 45 degrees away from the locking plane.

It should be noted that, for a typical nail made of steel where all locking holes point in the same direction, its locking holes may not be visible in the X-ray for a rotation (as in Step 5) beyond 30-35 degrees, meaning that a steel nail may not be localizable for rotations larger than 30-35 degrees. On the other hand, tools or implants made of, e.g., titanium absorb far less radiation than tools or implants made of, e.g., steel. Hence, for a titanium nail, tilted holes will lead to a gray-level gradient at the hole borders. This is shown in FIG. 18 for a rotation of 25 degrees away from the locking plane, and in FIG. 19 for a rotation of 45 degrees away from the locking plane. This effect means that it may be possible to localize tilted titanium nails for a much larger range of angles compared to steel nails. Another beneficial effect of titanium nails is that the drill, which is typically made of steel, may be visible against the nail. This may increase accuracy in localizing the drill when the drill tip is close to the nail, e.g., during drilling. It may also allow rotating the C-arm around a different axis, e.g., the propeller axis, where typically the X-ray shows the tip superpositioned on the nail.

If, in Step 5, the C-arm was rotated around the vertical axis instead of the C-axis, the system requires that the drill's tip lie in a plane whose normal is the nail axis and which contains the target trajectory. In this case, the drill tip's deviation from the target trajectory in AP direction may be computed.

Hence, an alternative to the above described workflow may be to acquire X-ray images from both a viewing direction obtained through rotating around the C-axis and a viewing direction obtained through rotating around the vertical axis, each away from the locking plane. In this case, no a priori information about the drill tip's position relative to the target trajectory is required. Hence, it is not required to position the C-arm in a true ML direction.

Example for a Potential Processing Workflow for Placement of Sacroiliac (SI) or Pedicle Screws Target object and target structure may also be anatomical. An example for an anatomical target structure is a pedicle. Concerning 3D reconstruction and relative 3D positioning and 3D orientation with respect to the tool, it may be sufficient to achieve the necessary accuracy for the target structure and hence the target trajectory.

The procedure is analogous to the distal locking procedure apart from localizing an anatomical target structure, which may proceed with or without a deterministic 3D model. A deterministic 3D model may be obtained either preoperatively (e.g., a preoperative CT scan) or intraoperatively (e.g., an intraoperative CT scan or O-arm). If a deterministic 3D model is not available, a statistical 3D model (e.g., a statistical shape or appearance model) may be used for 3D reconstruction, as discussed previously in the Section "3D reconstruction and localization of an anatomical object based on one X-ray image".

In this procedure, the tool may be unaffixed and manually held onto the target point of the anatomy and then approximately aligned with the target trajectory. Without acquiring a new X-ray image, the C-arm may be rotated, e.g., by 25 degrees around the C-axis. Following an iterative process as above, a new X-ray is acquired, and the system may compute the relative 3D position and 3D orientation between tool and target structure/object, taking into account that the tool's tip lies on the target trajectory. This assumes that the viewing angle onto the tool lies in a range that allows a sufficiently precise determination of 3D position and 3D orientation between both objects. If only a statistical model of anatomy is available, this step includes 3D reconstruction of the target structure/object.

In a next step, the system may compute the deviation between tool axis and target trajectory concerning angle deviation and, possibly, deviation in tip position in a direction parallel to the C-arm's rotation axis that was used for rotation between both images. The system may also compute the drill penetration depth. The system may provide this data to the user (e.g., in the form of two angle values, required translation for the tool's tip position, and remaining insertion depth). The user may then readjust the tool accordingly, acquire a new X-ray, and/or drill/insert the tool. The procedure also works if drilling had already commenced and the tool has already penetrated the anatomy because a priori information and side constraints remain unchanged.

Example for a Potential Processing Workflow for Determining 3D Position and 3D Orientation Between an Instrument and Anatomy, Based on Image Registration for Enhanced Accuracy By adjusting the bearing (translation and rotation) of a C-arm to be aligned with a particular part of anatomy (e.g., a narrow channel such as a pedicle), the tip of a tool (e.g., a drill, k-wire, or Jamshidi needle, or even an implant such as a screw) may be placed on a particular anatomical reference point. This step may be supported by the system by displaying the reference point in an acquired 2D X-ray image, or alternatively, the identification of the reference point by the surgeon may be used by the system to increase its accuracy. The C-arm is then rotated by, e.g., 20 to 30 degrees around the C-axis (or a comparable rotation around the propeller axis) while leaving the tool in place, and then another X-ray is acquired. The fact that the tool touches the surface of the anatomical object at the reference point may be used to reduce or even resolve the ambiguity introduced by the ambiguous localization of the tool. The C-arm movement relative to the previous image may then be determined, and the viewing direction onto the anatomical object may thus be determined with increased accuracy. Because this requires that the tool not move between X-ray images, it may be easier to affix the tool to anatomy, which may be done with the drill, but also with a Jamshidi needle or a k-wire.

Procedure

1. Based on a preoperative CT scan, a reference point and reference trajectory (i.e., intended drilling or insertion trajectory) and target end point may be planned before surgery. This may include planning an intended imaging direction for the C-arm, for instance, true lateral or true AP, or along pedicles or other easily recognizable landmarks. This Step 1 may also be performed intraoperatively (using an intraoperative 3D imaging device) by the system automatically and/or with user interaction.

2. During surgery, increased localization accuracy may be achieved by using a C-arm imaging direction either previously defined or computed online. The system may provide instructions to the user to help achieve the required C-arm bearing, for instance, by detecting the relative positions of certain anatomical features such as edges or points (see, e.g., the patent application by Blau filed on 23 Aug. 2018). The system may display the reference point in the X-ray image based on matching the structure or the entire object from the CT scan to the X-ray image. The surgeon then positions the tip of a tool (e.g., a drill, a Jamshidi needle, or a k-wire, or even an implant such as a screw) on this reference point, which may also be supported by the system by detecting the tool's tip in the 2D X-ray image. If necessary, the tool is intentionally held at an angle so that the tool (or a power tool) and the surgeon's hand do not occlude the view.

3. The tool is then approximately aligned with the desired direction.

4. The tool is affixed to the anatomical structure, if possible with a defined marking on the tool so that the precise penetration depth may be determined.

5. Another X-ray from the same imaging direction is acquired. Now, the position of the tool's tip is restricted because it lies approximately on the drilling or insertion trajectory. If the tool's penetration depth is known precisely, there is less ambiguity than if the tool's penetration depth is not known. The system may check (e.g., by image difference analysis) whether the anatomy shown in the X-ray image remains unchanged. Alternatively, in this step, it may also be sufficient for the user to indicate in which plane (relative to anatomy) the tool's tip lies. If Step 5 cannot be performed because the tool or the surgeon's hand would occlude the view, Steps 4 and 5 would be performed without aligning the tool in Step 3.

6. The C-arm is moved or rotated into a different position. Based on the localized and affixed tool, the C-arm movement relative to the previous image may be determined. Together with the localized anatomy, this allows a determination of the relative 3D position and 3D orientation between tool and anatomy. Quantities to be determined may be jointly optimized.

7. If the tool has such a small diameter that it may be localized with sufficient precision only for certain angles, then the tool must be viewed at a suitable angle (e.g., within the range of 10 to 55 degrees) in all acquired X-ray images to be registered. Moreover, anatomical structures may also be localized more precisely for specific imaging directions. Hence, accuracy for determining relative 3D position and 3D orientation in Step 7 may be increased by choosing a particular imaging direction onto anatomy. However, because such special imaging directions are typically true AP and true ML, this means that the angle between the two X-ray images is close to 90 degrees. Moreover, it must already be observed when affixing the tool in Step 4 that the tool's tip will be viewed at a suitable angle (e.g., within the range of 10 to 55 degrees) in all X-ray images to be acquired and registered. Therefore, in such a case, an appropriate angle for affixation of the tool would be in the middle between the viewing directions true AP and true ML, i.e., approximately 45 degrees.

8. Once an X-ray has been acquired and above conditions are satisfied, the system may then compute the deviation between the tool's axis and the reference trajectory, which it may provide to the user (e.g., by displaying two angle values). The user may then withdraw the tool to the original reference point and realign it with the reference trajectory. The system may help the user find the original reference point.

Reaching the correct reference trajectory may require an iterative process acquiring further X-rays. After a new X-ray is acquired, the system may then check (e.g., through an image difference analysis) whether the anatomy is still shown in the X-ray in the same orientation and position. If this is the case, the relative 3D position and 3D orientation between tool and anatomy may again be computed because of the a priori information that the tool's tip lies on the reference trajectory. Furthermore, the system may also calculate the penetration depth, in this case, e.g., the distance between tool's tip and target end point, and thus inform the user. During tool insertion, further X-rays may be acquired and above steps may be repeated.

If it is not feasible or desired to ensure the tool is viewed within a suitable angle range (e.g., 10 to 55 degrees) in every acquired X-ray, the power tool holding the tool (e.g., a power drill holding the drill) may also be removed (obvious in case of using a k-wire or Jamshidi needle). If the entire tool (tip and bottom end) is visible in the X-ray image, the length of the tool's projection in the X-ray image may be determined and thus allow localizing the tool with sufficient accuracy. In such a case, the tool may even be viewed at an angle close to 90 degrees. This would allow affixing the tool initially at approximately the correct angle (eliminating the need to first affix the tool intentionally at an incorrect angle, cf. Step 7), thus reducing the number of required iterations in Step 8.

For the insertion of a pedicle screw, it may be possible to identify the entry point of the pedicle in an AP view in which the pedicle axis is inclined by, e.g., 10 to 45 degree relative to the viewing direction. In such an imaging direction, the drilling machine does not occlude the view and there is no need to acquire a second image from another direction after positioning the tip of the instrument on the entry point of the anatomical structure and aligning the angle of the tools axis with the target trajectory. As this procedure often involves a k-wire or a Jamshidi needle, the tool may be affixed to the bone with its axis already aligned with the desired target trajectory.

If necessary, the user may then acquire one or more X-ray image from other viewing angles, which the system may use to perform above described image registration to enhance accuracy. If still needed, the drilling angle may be further optimized based on the additional information (possibly without withdrawing the drill) and drilling may proceed. Due to the fact that the other pedicle in this first AP view has a mirrored inclination to the first pedicle (cf. FIG. 15 showing two Jamshidi needles 15.JN and 15.JN2), it is possible to repeat the procedure above for the other pedicle of the same vertebra and make use of the already inserted Jamshidi needle (by using it's projection in the x-ray image) of the first pedicle to allow a more robust registration of images.

Figure 24:
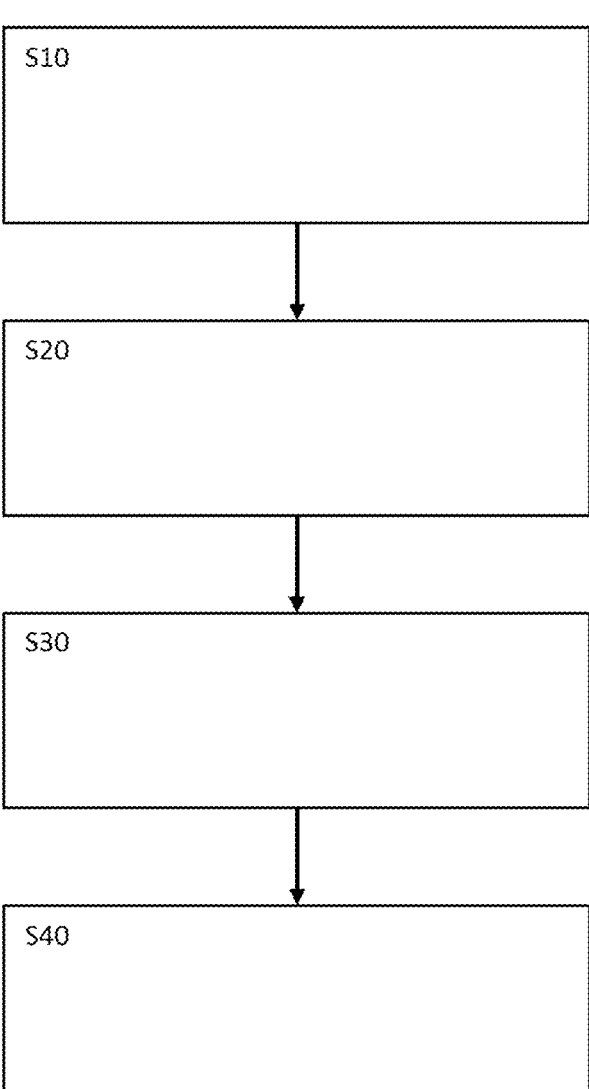
FIG. 24 shows a general workflow for the proposed procedures.
Figure 25:
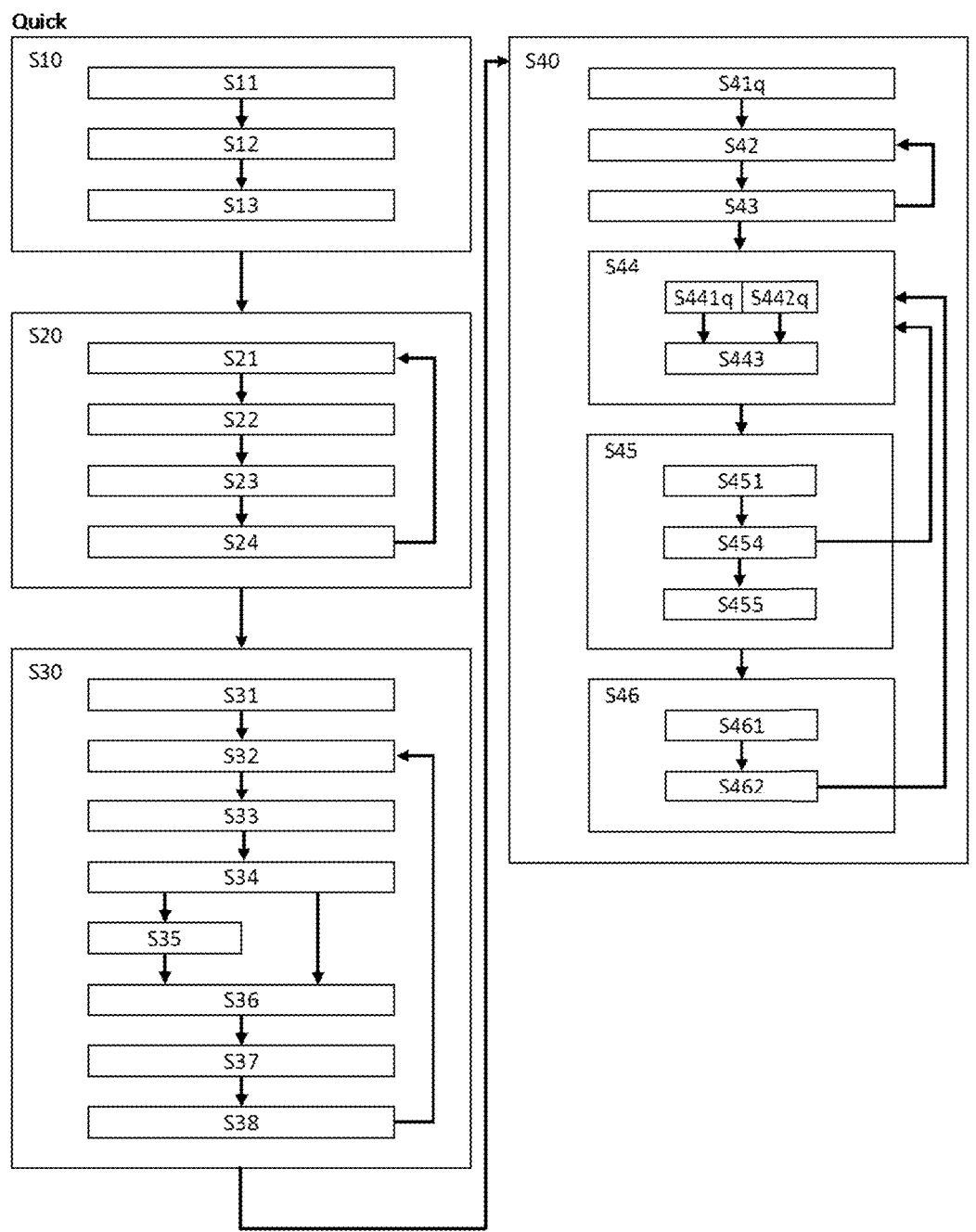
FIG. 25 shows details for a quick implementation of the general workflow in FIG. 24.
Figure 26:
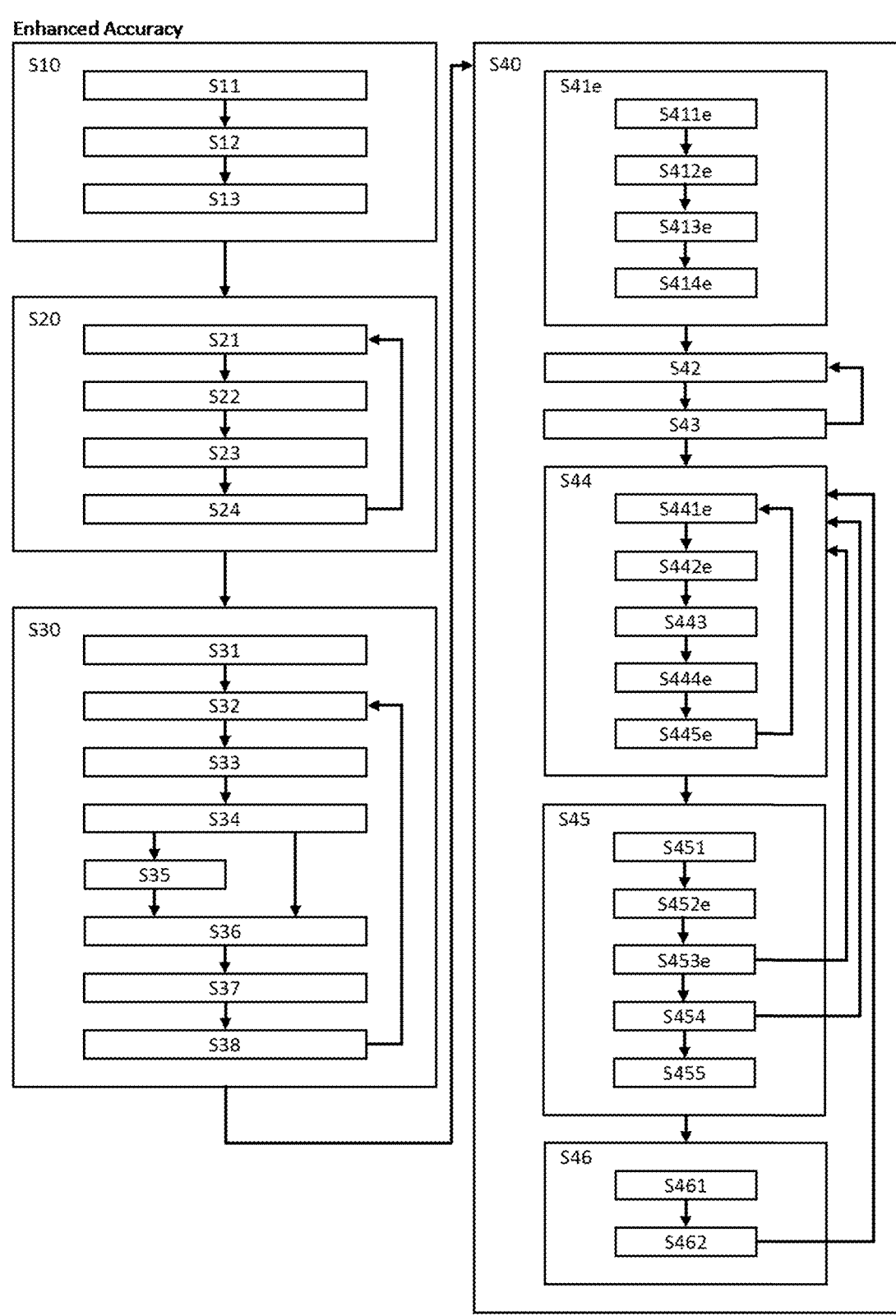
FIG. 26 shows details for an enhanced-accuracy implementation of the general workflow in FIG. 24.

Flowchart of FIGS. 24-26

FIG. 24 shows a general flowchart that covers all of the procedures presented in the sections "Example for a potential processing workflow for a distal locking procedure", "Example for a potential processing workflow for placement of sacroiliac (SI) or pedicle screws", and "Example for a potential processing workflow for determining 3D position and 3D orientation between an instrument and anatomy, based on image registration for enhanced accuracy" above. There are two possible implementations: a quick implementation, shown in FIG. 25, which is applicable for the procedures presented in the sections "Example for a potential processing workflow for a distal locking procedure" and "Example for a potential processing workflow for placement of sacroiliac (SI) or pedicle screws" above; and an implementation for enhanced accuracy, shown in FIG. 26, which is applicable for the procedure presented in the section "Example for a potential processing workflow for determining 3D position and 3D orientation between an instrument and anatomy, based on image registration for enhanced accuracy" above.

It will be appreciated by a person skilled in the art that not all steps must be performed and that further sub-steps might practically be performed which are not mentioned, dependent on the circumstances of a concrete application of the teaching provided herein.

The steps in FIGS. 24, 25, and 26 are:

S10: Generate and load 3D model.

S11: Pre-operative planning (optional).

S12: Load entire 3D model.

S13: Intra-operative automatic determination of target trajectory (trajectories)/plane (planes) and, if applicable, target point (e. g., in case of anatomy).

S20: Support for C-arm adjustment.

S21: Acquire X-ray image.

S22: Support to reach special viewing direction onto target object, e. g., circular hole (potentially supported by localization of nail), or true AP/ML view onto anatomy (potentially supported by DNN), by, e.g., providing rotation angle (including direction) around C-axis, rotation around propeller axis, etc.

S23: If ambiguities occur, system provides only values of rotation angles without direction.

S24: If viewing direction is not sufficiently close to desired viewing direction, user follows system instructions and continues with S21. If corresponding 3D model of anatomy (e.g., CT-scan, i.e., deterministic) is available, the desired viewing direction may differ from target trajectory because in this case it is possible to obtain the target trajectory from the current viewing direction and the 3D model, knowing that the tip of the opening tool will be placed on the anatomy. Example: distal locking, where the opening tool is placed on the femur and a 3D model of the femur is available. After localizing the target object (S33), the system calculates the intersection point of the target trajectory of the nail model with the surface of the femur model. Using the 3D model of the anatomy, the system provides adjustment instructions for the opening tool tip (S37).

S30: Support for opening tool positioning.

S31: Positioning of opening tool.

S32: Acquire X-ray image.

S33: Localization of target object/structure.

S34: If target trajectory is sufficiently aligned with viewing direction, the target point is directly visible in 2D X-ray (1 DoF for tool tip position undefined). Go to S36.

S35: System displays intersection point of 3D surface of anatomy (also with distal locking) and target trajectory, superpositioned onto 2D X-ray (all DoF for tool tip position defined).

S36: 2D match of opening tool.

S37: System provides user instructions to support opening tool's tip adjustment.

S38: If position not reached with sufficient accuracy, user follows system instructions, and continues with S32.

S40: Determine 3D position and orientation between opening tool and target object in order to align opening tool with target trajectory.

S41e: Opening tool fixation needed.

S411e: Opening tool fixation. In case it is intended to apply S44, system provides support to affix opening tool to target object at an angle that ensures that the angle between the opening tool and all special viewing directions is less than 65 degrees. Two angle values are provided. If user acquires another image from the same viewing direction, fixation angle of opening tool is validated by system.

S412e: Acquire X-ray image without change in relative position between C-arm and anatomy.

S413e: Image difference analysis to determine entry depth of opening tool.

S414e: Determine 3D position and 3D orientation of opening tool relative to anatomy.

S41q: No opening tool fixation. Unsupported aiming for trajectory by user.

S42: System calculates and displays adjustment values for C-arm rotation in order to reach a 25-degree angle between viewing direction and target trajectory. If ambiguities occur, system provides only values of rotation angles without direction.

S43: User positions C-arm according to displayed adjustment values and acquires X-ray image. If viewing direction is not sufficiently close to desired viewing direction from S42, go to S42.

S44: Calculate 3D position and 3D orientation between target object and opening tool for final opening tool adjustment instructions.

S441e: In case of iterative optimization, 3D localization of opening tool and calculation of transformation matrix between 3D position and 3D orientation of opening tool between current image and previous special viewing direction.

S442e: Potentially improved 3D orientation and 3D position of anatomy based on (i) above transformation matrix (S441e), (ii) all previous 3D orientations and 3D positions of anatomy with current opening tool position, and (iii) the current 3D orientation and 3D position of anatomy (either iterative or joint optimization).

S441q: In case of iterative optimization, localization of target object. Determine 3D position and 3D orientation between opening tool and target object based on localization of target object and the a priori information that opening tool's tip is positioned on target trajectory/plane. Go to 443.

S442q: Joint optimization of 3D orientation and 3D position of target object relative to opening tool.

S443: Validate and correct a priori information (opening tool's tip position relative to target object), e. g., in case nail's distal-proximal deviation can be validated and corrected.

S444e: If accuracy of 3D position and 3D orientation between anatomy and opening tool needs further improvement, system calculates and displays adjustment values for C-arm rotation in order to reach a further special viewing direction.

S445e: User positions C-arm according to displayed adjustment values and acquires X-ray image. If viewing direction is not sufficiently close to desired viewing direction, go to S44.

S45: User moves opening tool by the provided adjustment values in order to align opening tool with target trajectory.

S451: Since 3D model of target object provides the target trajectory, system provides angles to adjust the direction of opening tool (two angles including directions) in order to align the tool with the target trajectory, gained from above determined 3D position and 3D orientation of tool relative to target object.

S452e: If opening tool is still fixated in first position (S41e), user withdraws opening tool until its tip is on target trajectory, then aligns opening tool based on system output, acquires X-ray image. (Alternatively, a second opening tool is used to aim for the target trajectory. In this case go to S44.)

S453e: System compares images (e.g., by image difference analysis). If images are locally (for the target object) close enough, go to S44.

S454: In case alignment of opening tool with target trajectory is not close enough, user aligns opening tool based on system output, acquires X-ray image, and continues with S44.

S455: In case remaining alignment instruction provides small enough values, system displays information how far to drill. User may align opening tool based on alignment instruction and decides whether he/she acquires another X-ray image.

S46: Drilling.

S461: User drills.

S462: Whenever user wants to validate drill direction or drill depth, he/she acquires new X-ray and continues with S44.

It is noted that in case the system is able to give instructions on how to adjust the tool's orientation (and possibly position) already in the first X-ray image, these may be used to reach a provisional alignment of the tool with the target trajectory. If, after this alignment, the tool's tilt is already within the required range of angles and neither power tool nor surgeon's hand occlude the view, another image from a different imaging direction may not be required, and a validation of the applied instructions (regarding tool's orientation and possibly position) may be done, if necessary, with an X-ray from the same imaging direction. Another X-ray image may not be necessary if (i) no correction or only a very small correction would be necessary, or (ii) an apparatus is used which ensures a sufficiently precise application of given instructions. Such an apparatus could be a manual apparatus or a robot.

As described in the section "Method for positioning a target object/structure in the C-arm's field of view from a desired viewing direction", a perfect alignment of the C-arm in the direction of the target trajectory may not be required, especially if the tool is placed on the target object and the target point is identifiable in the current X-ray. It may be possible that all the necessary information to compute relative 3D positions and 3D orientations is already available in the very first X-ray image. Hence, depending on the setup, the first X-ray image may suffice to perform the entire distal locking procedure. An example of such a setup would be the employment of a robot that holds the tool at a given point already considering the required tilt. If it is possible to identify both target trajectory and the necessary starting point already in the first acquired X-ray image and to determine 3D position and 3D orientation between tool and target object, the robot may translate and rotate the tool, as required, and drill. In the general case, where target trajectory and resulting starting point for drilling may not be identified based on the first X-ray, another X-ray may be acquired from a different suitable viewing direction. Both X-ray images may be registered based on localizing the target object, which may allow computing the 3D position and 3D orientation of the tool relative to the target object, and thus also relative to the target trajectory. Hence, the entire repositioning (translation and rotation) including drilling may be performed by a robot. This procedure is not limited to drills.

Reduction Support

When anatomically reducing a fracture of the proximal femur, it may happen that, even though the reduction looks correct in both an AP X-ray image (e.g., Adam's bow looks intact) and a lateral image, there is nevertheless a remaining dorsal gap. For this reason, it may be recommended to acquire a true ML X-ray image because a true ML image has the largest chance of showing such a gap. However, it is still possible that even a true ML image does not reveal such an incorrect reduction.

Yet a remaining dorsal gap that is not visible in an X-ray has limited degrees of freedom, meaning that the incorrect reduction must be correctable by rotating the medial fragment around the axis defined by the main fracture line.

Such a correction may be achieved by the following procedure, which is presented here for the case of two fragment pieces.

1. The system loads a 3D model (typically obtained using a preoperative CT scan) showing the segmented 3D bone fragments.
2. The surgeon acquires an AP X-ray image.
3. The system may optionally detect the fracture line as a reference.
4. The system may optionally determine a line approximating the main fracture line.
5. The surgeon reduces the fracture until it is deemed correct in an AP X-ray image.
6. The surgeon rotates the C-arm into an ML position and acquires an X-ray image.
7. The system may determine the relative 3D position and 3D orientation between the two bone fragments, and may thus support the surgeon in evaluating the reduction and potentially determining a correct reduction.

For Step 7, the system may use the a priori information that the bone fragments are touching each other along the anterior fracture line. This line is actually defined in 3D, hence the detection in Step 3 above is only optional.

In this scenario, two objects (the fragments) are in contact not just at a single point but along a one-dimensional structure approximating a line in 3D space. Hence, there is only one degree of freedom (i.e., the rotation around the anterior fracture line) that is not defined. Hence, a determination of the relative 3D position and 3D rotation between the objects is possible using the ideas presented in previous sections.

A combination of this method with other previously described techniques (i.e., registration of a multiplicity of X-ray images with or without additional instrument/implant (e.g., nail) in the X-ray) may lead to a higher accuracy. This may not even require any additional efforts, if done after inserting the nail, which may be used to help register both images.

It is noted that this type of a priori information exists in several reduction scenarios in orthopedic trauma, e.g., in a determination of the varus/valgus position of fragments. Further examples may pertain to scenarios where it is known (e.g., based on an X-ray):

that fragments are touching each other (the least restrictive type of a priori information)

where fragments are touching each other; it may be sufficient to know that the location is in one of several possibilities: e.g., if a reduction looks correct in an AP X-ray image, it may be assumed that the fragments are in contact along the fracture line either in dorsal or ventral direction; in a more extreme scenario, the dorsal fracture line of one fragment may touch the ventral fracture line of another fragment; an algorithm may then evaluate all these possibilities and choose the one that provides the best 3D match how the fragments are touching each other (in a point, a 1D structure such as a line, or a 2D structure such as a plane, etc.)

It is noted that the procedure presented above may also be applied to more than two fragments. If there are known relations between bone fragments A and B, and there are known relations between bone fragments B and C, this may be used to relate bone fragments A and C.

The system may also automatically determine whether any detected anatomical gaps between bone fragments are within norms, and whether any protruding bone fragments are statistically significant because they deviate significantly from a fitted statistical shape model.

Figure 27:
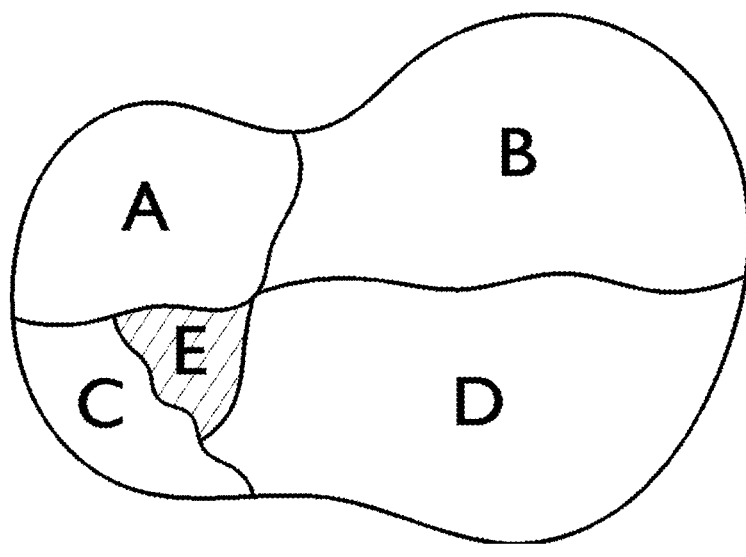
FIG. 27 shows an axial view onto the proximal end of the tibia.

A further example where a surgeon might incorrectly believe that a reduction is correct, based on what is seen in X-ray images, is a multi-fragment scenario of the proximal tibia. FIG. 27 shows an axial view onto the proximal end of a tibia with fragments A through E. Here, the fragments labeled A through D are already anatomically reduced, but fragment E has sunk, i.e., is moved in distal direction compared to a correct anatomical reduction. Such a situation may be difficult to determine for a surgeon because an X-ray (in AP or ML direction) will show many other fracture lines and also lines corresponding to regular anatomy (e.g., a fibula). The present invention may be able to detect such a scenario by correctly determining the relative 3D positions and 3D orientations between all fragments. This may be possible because the system may use the a priori information that all fragments are anatomically reduced possibly except for inside fragments (such as fragment E in FIG. 27), which may have been moved in distal direction. Here, the free parameter for the system would be the proximal/distal position of fragments located in the interior of the bone.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A system for processing X-ray images, the system comprising:

a processing unit and a software program product, wherein, when the software program product is executed by the processing unit, wherein the processing unit is configured to:

receive an X-ray image, the X-ray image being a projection image of a first object and a second object, wherein a robot holds the second object and is configured to adjust a position, an orientation or a combination thereof of the second object, localize the first object in the X-ray image, wherein the localizing includes a determination of the 3D orientation of the first object and a determination of the 2D spatial position of the projection of the first object onto an image plane, localize the second object in the X-ray image, wherein the localizing includes a determination of the 3D orientation of the second object and a determination of the 2D spatial position of the projection of the second object onto the image plane, and determine a relative 3D position and 3D orientation between the first object and the second object based on (i) the X-ray image, (ii) the localization of the first object, and (iii) the localization of the second object.

2. The system of claim 1, wherein the relative 3D position and 3D orientation between the first object and the second object is further based on knowledge about a spatial relation between a selected point of the second object and a geometrical aspect of the first object, wherein the geometrical aspect of the first object is an aspect out of the group consisting of a plane, a line, a point, an axis, a trajectory, an outline, a curvature, a center point, a one-dimensional manifold, a two-dimensional manifold, or a combination thereof.

3. The system of claim 2, wherein the selected point of the second object includes a plurality of selected points of the second object.

4. The system of claim 2, wherein the first object is a bone implant inserted in a bone, wherein the knowledge about the spatial relation between the selected point of the second object and the geometrical aspect of the first object is obtained (i) by registration of a further X-ray image with the X-ray image, wherein both X-ray images show both the first and the second object, and (ii) by the knowledge that the point of the second object is at the same 3D position relative to the first object in both X-ray images.

5. The system of claim 4, wherein an at least partial 3D reconstruction of the bone surface and its position relative to the first object is determined based on (i) the registration of the further X-ray image with the X-ray image, (ii) a detection of bone edges in both X-ray images, and (iii) the knowledge that the point of the second object is positioned at the bone surface.

6. The system of claim 2, wherein the geometrical aspect of the first object is a plane or a line and wherein the X-ray image is generated with an imaging direction being inclined relative to the geometrical aspect with an angle in a range between 10 degrees and 65 degrees, preferably in the range between 20 degrees and 30 degrees.

7. The system of claim 2, wherein the selected point of the second object is a distal tip of the object and wherein the information of the 3D location of said distal tip is a point of contact of the distal tip with a surface of the first object.

8. The system of claim 1, wherein the first object is a bone implant inserted in a bone, wherein the knowledge about the spatial relation between the selected point of the second object and the geometrical aspect of the first object is obtained (i) by an at least partial 3D reconstruction of a bone surface of the bone with known spatial relation to the geometrical aspect of the first object and (ii) by the knowledge that the selected point of the second object is positioned at the bone surface.

9. The system of claim 1, wherein the processing unit is further caused to determine a deviation of the 3D position and 3D orientation of the second object from an intended spatial relation of the second object relative to the first object.

10. The system of claim 1, wherein the first object is an aspect of an anatomy or a first implant and wherein the second object is an aspect of an anatomy, a tool or a second implant.

11. The system of claim 1, wherein the system further comprises a device for providing information to a user, wherein the information includes at least one information out of the group consisting of X-ray images and instructions regarding step of a procedure.

12. The system of claim 1, the system further comprising a C-arm based X-ray imaging device for generating the X-ray image.

13. The system of claim 12, wherein the C-arm based X-ray imaging device includes a robotic C-arm, wherein the software program product is further configured to adjust the robotic C-arm.

14. The system of claim 12, wherein the C-arm based X-ray imaging device includes a robotic C-arm, wherein the software program product is further configured to acquire another X-ray image with the robotic C-arm.

15. The system of claim 1, wherein the processing unit is further configured to perform drilling in a bone using the robot.

16. The system of claim 15, wherein the treatment of the bone includes at least one out of the group of inserting an implant, inserting a screw, inserting a K-wire, drilling, performing an incision, performing a reduction of a fracture.

17. The system of claim 1, wherein the determination of the relative 3D position and 3D orientation between the first object and the second object is further based on knowledge about a spatial relation between a selected point of the second object and a geometrical aspect of the first object.

18. The system of claim 1, wherein the first object is an aspect of an anatomy.

19. The system of claim 1, wherein the second object is a tool.

* * * * *